(12) United States Patent
Wolfe et al.

(10) Patent No.: US 12,138,312 B2
(45) Date of Patent: Nov. 12, 2024

(54) CELL-PENETRATING PEPTIDES FOR ANTISENSE DELIVERY

(71) Applicants: Sarepta Therapeutics, Inc., Cambridge, MA (US); Massachusetts Institute of Technology, Cambridge, MA (US)

(72) Inventors: Justin M. Wolfe, Cambridge, MA (US); Colin M. Fadzen, Cambridge, MA (US); Zi-Ning Choo, Cambridge, MA (US); Rebecca L. Holden, Cambridge, MA (US); Monica Yao, Cambridge, MA (US); Gunnar J. Hanson, Cambridge, MA (US); Bradley L. Pentelute, Cambridge, MA (US)

(73) Assignees: Sarepta Therapeutics, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 716 days.

(21) Appl. No.: 16/756,616

(22) PCT Filed: Oct. 17, 2018

(86) PCT No.: PCT/US2018/056205
§ 371 (c)(1),
(2) Date: Apr. 16, 2020

(87) PCT Pub. No.: WO2019/079386
PCT Pub. Date: Apr. 25, 2019

(65) Prior Publication Data
US 2020/0316210 A1    Oct. 8, 2020

Related U.S. Application Data

(60) Provisional application No. 62/573,379, filed on Oct. 17, 2017.

(51) Int. Cl.
| | |
|---|---|
| *A61K 47/65* | (2017.01) |
| *A61K 31/713* | (2006.01) |
| *A61K 47/64* | (2017.01) |
| *C12N 15/11* | (2006.01) |
| *C12N 15/113* | (2010.01) |

(52) U.S. Cl.
CPC ............ *A61K 47/65* (2017.08); *A61K 31/713* (2013.01); *C12N 15/111* (2013.01); *C12N 15/113* (2013.01); *A61K 47/6455* (2017.08); *C12N 2310/11* (2013.01); *C12N 2310/3513* (2013.01)

(58) Field of Classification Search
CPC ...... C12N 2310/3233; C12N 2310/314; A61K 47/545; A61K 47/6455
See application file for complete search history.

(56) References Cited

U.S. PATENT DOCUMENTS

| | | | |
|---|---|---|---|
| 2009/0088562 A1 | 4/2009 | Weller et al. | |
| 2012/0289457 A1 | 11/2012 | Hanson | |
| 2015/0080311 A1 | 3/2015 | Moulton et al. | |
| 2015/0238627 A1 | 8/2015 | Leger et al. | |
| 2017/0165290 A1 | 6/2017 | Dong et al. | |
| 2021/0260206 A1* | 8/2021 | Pentelute | A61K 47/64 |

FOREIGN PATENT DOCUMENTS

| | | |
|---|---|---|
| WO | WO 2009/005793 A2 | 1/2009 |
| WO | WO 2012/150960 A1 | 4/2009 |
| WO | WO 2014/124952 A1 | 8/2014 |
| WO | WO 2017/066789 A1 | 4/2017 |

OTHER PUBLICATIONS

Zhou. Bioorganic and Medicinal Chemistry, 2006, 14, 7862-7874 (Year: 2006).*
Extended European Search Report for European Application No. 18868379.1 mailed Jul. 14, 2021, 8 pages.
International Preliminary Report on Patentability for International Application No. PCT/US2018/056205 mailed Apr. 21, 2020, 6 pages.
International Search Report and Written Opinion for International Application No. PCT/US2018/056205 mailed Dec. 21, 2018, 9 pages.
Wolfe et al., "Machine Learning to Predict Cell-Penetrating Peptides for Antisense Delivery", *ACS Central Science* 4(4):512-520, Apr. 25, 2018.

* cited by examiner

*Primary Examiner* — Noble E Jarrell
(74) *Attorney, Agent, or Firm* — Sterne, Kessler, Goldstein & Fox P.L.L.C.

(57) ABSTRACT

Provided herein are oligonucleotides, cell penetrating peptides, and peptide-oligonucleotide-conjugates. Also provided herein are methods of treating a muscle disease, a viral infection, or a bacterial infection in a subject in need thereof, comprising administering to the subject oligonucleotides, peptides, and peptide-oligonucleotide-conjugates described herein.

19 Claims, 5 Drawing Sheets
Specification includes a Sequence Listing.

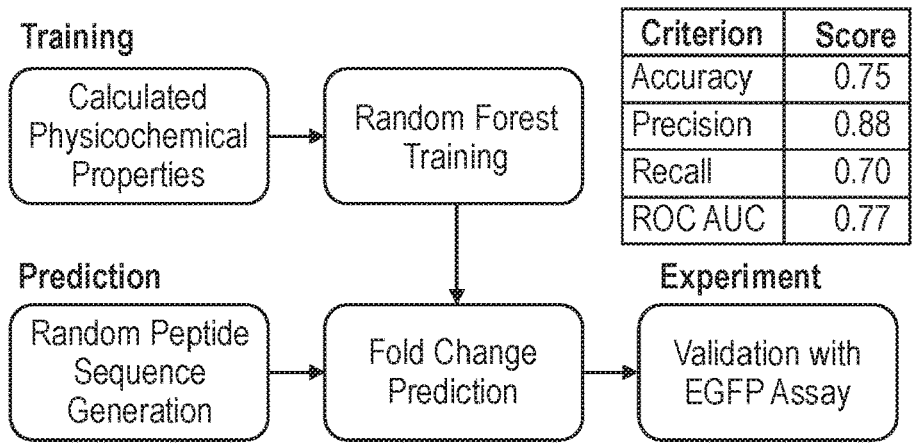
*Fig. 2A*
| Name | Sequence | Theoretical Net Charge | Predicted Fold Change > 3 | Experimental Fold Change |
|---|---|---|---|---|
| PPC1 | KQPRIPKRKK | 6 | Yes | 3.4 |
| PPC2 | LKKRRKLPKKKPIRNEQ | 8 | Yes | 3.3 |
| PPC3 | KKYRGRKRHPR | 8 | Yes | 4.4 |
| PPC4 | APKRKKLKKRF | 7 | Yes | 4 |
| PPC5 | GRAARAPGRRKQ | 5 | Yes | 3.5 |
| NS1 | HDLPKGG | 1 | No | 0.9 |
| NS2 | AGSHRRL | 3 | No | 1.8 |
*Fig. 2B*
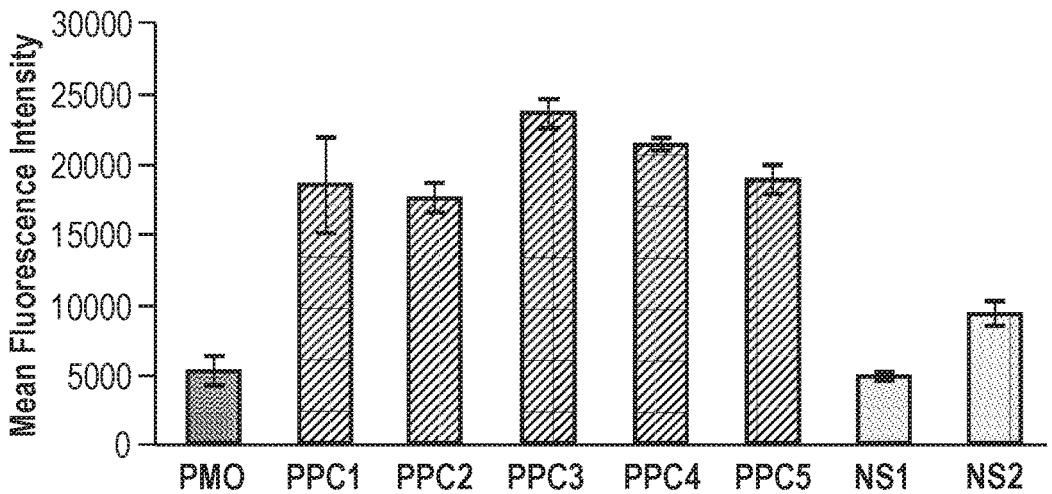
*Fig. 2C*

CELL-PENETRATING PEPTIDES FOR ANTISENSE DELIVERY

CROSS-REFERENCE TO RELATED APPLICATIONS

This application is a 35 U.S.C. § 371 National Phase Application of PCT/US2018/056205, filed Oct. 17, 2018, which claims priority to U.S. Provisional Application Ser. No. 62/573,379, filed Oct. 17, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 31, 2018, is named 606054_SPT-010PC_SL.txt and is 20,420 bytes in size.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing or translation through any one of a number of antisense mechanisms. The sequence specificity of antisense compounds makes them attractive as tools for target validation and gene functionalization, as well as therapeutics to selectively modulate the expression of genes involved in disease.

Although significant progress has been made in the field of antisense technology, there remains a need in the art for oligonucleotides and peptide-oligonucleotide-conjugates with improved antisense or antigene performance.

SUMMARY

Provided herein are peptide-oligonucleotide-conjugates comprising an oligonucleotide covalently bound to a cell-penetrating peptide (CPP). Also provided herein are methods of treating a disease in a subject in need thereof, comprising administering to the subject a peptide-oligonucleotide-conjugate described herein.

Accordingly, in one aspect, provided herein is a peptide-oligonucleotide-conjugate of Formula I:

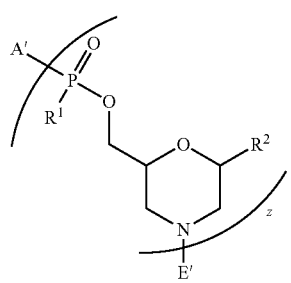

(I)

or a pharmaceutically acceptable salt thereof, wherein A' is

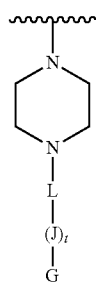

or E' is

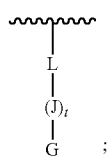

wherein L is covalently linked by an amide bond to the amino-terminus of J, and L is —C(O)(CH$_2$)$_{1-6}$—C$_{1-6}$-heteroaromatic-(CH$_2$)$_{1-6}$C(O);

each J is, independently at each occurrence, selected from the group consisting of arginine, glycine, leucine, alanine, phenylalanine, methionine, tryptophan, lysine, glutamine, glutamic acid, serine, proline, valine, isoleucine, cysteine, tyrosine, histidine, asparagine, aspartic acid, and threonine; and t is 5-27;

wherein at least one J is arginine.

In one embodiment, L is —C(O)(CH$_2$)$_{1-6}$-triazole-(CH$_2$)$_{1-6}$C(O).

In one embodiment, the peptide-oligonucleotide-conjugate of Formula I is a peptide-oligonucleotide-conjugate of Formula Ia:

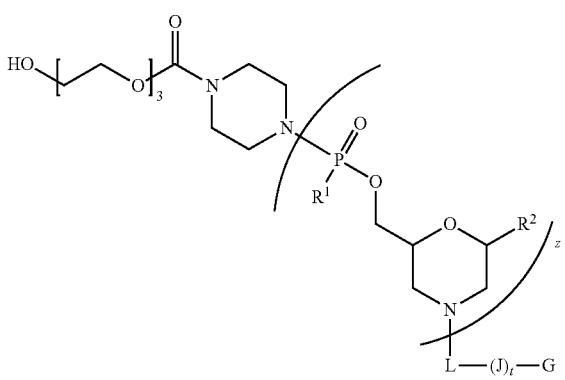

(Ia)

or a pharmaceutically acceptable salt thereof, wherein (J)$_t$-G is a cell-penetrating peptide as defined above.

In another embodiment, the peptide-oligonucleotide-conjugate of Formula I is a peptide-oligonucleotide-conjugate of Formula Ib:

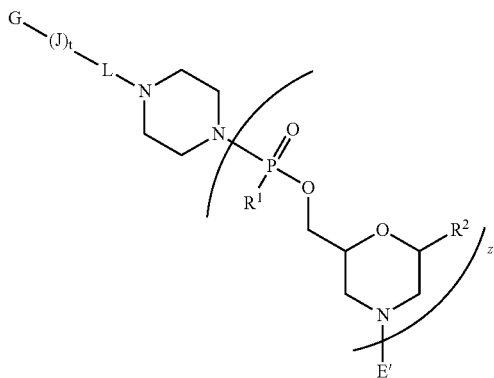

or a pharmaceutically acceptable salt thereof,
wherein $(J)_t$-G is a cell-penetrating peptide as defined above.

In still another aspect, provided herein is a method of treating a muscle disease, a viral infection, or a bacterial infection in a subject in need thereof, comprising administering to the subject a peptide-oligonucleotide-conjugate of the present disclosure.

BRIEF DESCRIPTION OF THE FIGURES

FIG. 2A Shows the scheme of the workflow for the development of computationally derived peptide sequences for antisense delivery, as well as the performance metrics of the model based on the test set. FIG. 2B Shows a table of five predicted PMO carriers (PPC) and two predicted negative sequences (NS) (SEQ ID NOs. 66-72, respectively, in order of appearance). FIG. 2C Shows the mean fluorescence intensity of eGFP HeLa cells treated at a concentration of 5 µM with each of the PPCs and NSs in serum-containing media.

DETAILED DESCRIPTION

Figure 1A:
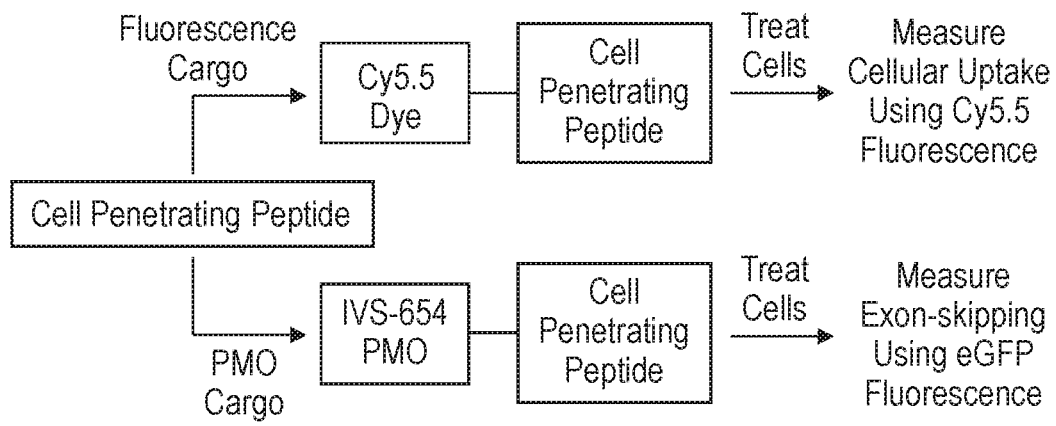
FIG. 1A Shows a workflow for comparing CPP effectiveness with either a fluorophore attached or a functional PMO for exon-skipping.
Figure 1B:
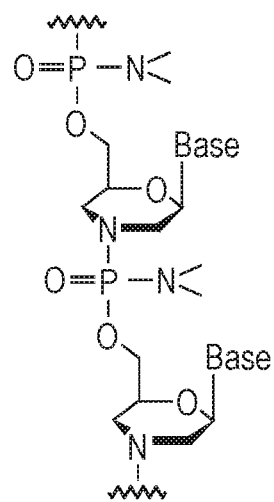
FIG. 1B Shows the basic structure of PMOs, a type of antisense oligonucleotide.
Figure 1C:
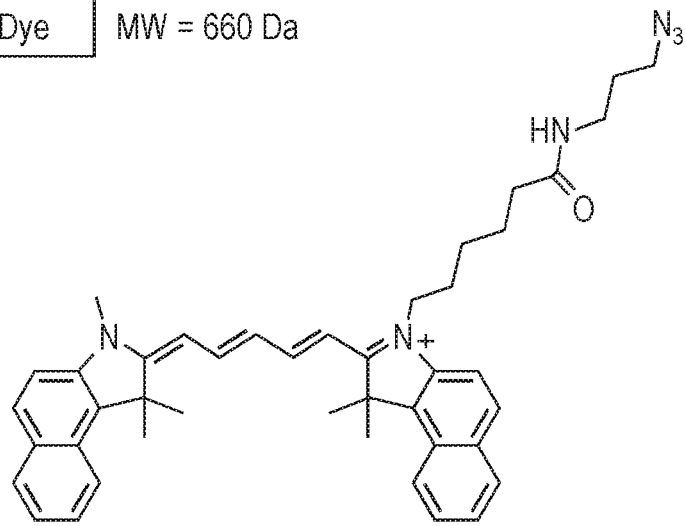
FIG. 1C Shows comparison of the structures of PMO (SEQ ID NO.: 65) and Cy5.5 as provided herein.
Figure 1D:
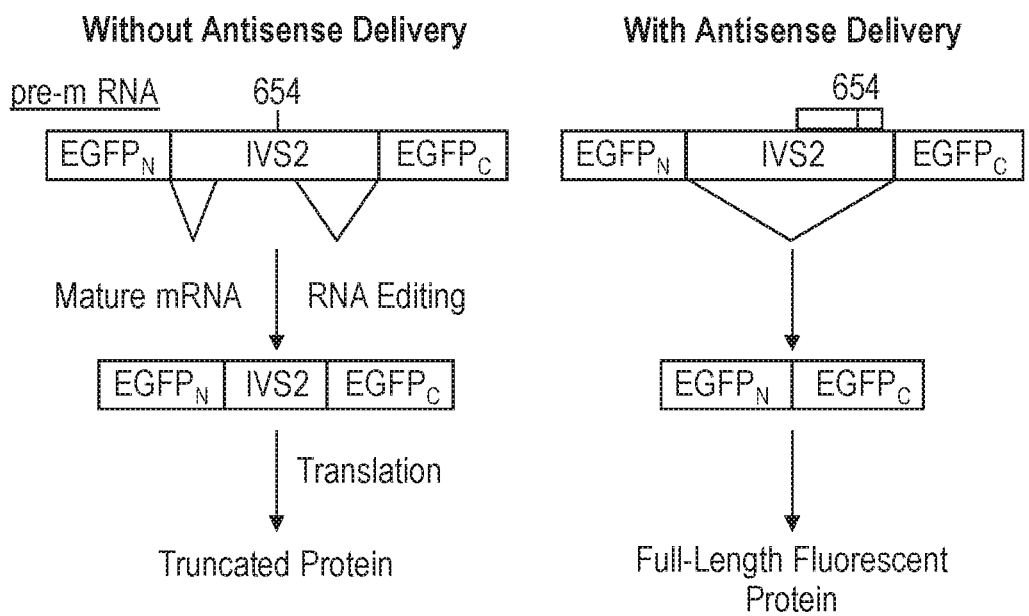
FIG. 1D Shows the description of the eGFP assay for functional exon-skipping.

The efficient intracellular delivery of many pharmaceutically active compounds, such as proteins and nucleic acids, is an outstanding challenge in the field of drug delivery. Many large macromolecules are unable to cross the plasma membrane, and often end up trapped in endosomes and degraded in lysosomes. Over the past few decades, multiple approaches have been developed to promote the cytosolic delivery of large macromolecules, including supercharging the molecules with a high density of charge, complexing the molecules with delivery vehicles such as liposomes or nanoparticles, and conjugating to cell-penetrating peptides. Since the discovery that a twenty amino acid fragment of the trans-activating transcriptional activator (TAT) from HIV-1 enabled a protein to cross the plasma membrane, hundreds of cell-penetrating peptides (CPPs) have been reported to improve entry into the cytoplasm. These peptides have been derived from many natural sources, such as viral proteins, DNA-binding proteins, signal peptides, and antimicrobial peptides. Additionally, CPPs have been rationally designed and identified from DNA-encoded peptide libraries. CPP sequences exhibit a wide diversity of physicochemical properties and range from highly cationic to amphipathic to hydrophobic. To confirm that a peptide is a cell-penetrating peptide, traditional experiments have included flow cytometry and live-cell confocal imaging using a fluorophore-labeled CPP (see, for example, FIG. 1A, FIG. 1B, FIG. 1C, FIG. 1D, FIG. 1E, and FIG. 2C). While these experiments provide evidence of cell penetration, they fail to address the question of whether the CPP is suitable for the delivery of a particular macromolecular cargo. In spite of that, CPPs have been utilized to improve the cellular delivery of peptides, enzymes, antibodies, oligonucleotides, nanoparticles, and chemotherapeutics.

One promising application of CPPs is for the delivery of phosphorodiamidate morpholino oligonucleotides (PMO). PMOs are a charge-neutral antisense therapeutic in which the ribose sugar is replaced with a methylenemorpholine ring and the phosphodiester backbone is replaced with a phosphorodiamidate backbone. PMOs bind to pre-mRNA and can alter gene splicing through a process known as "exon-skipping." Recently, the PMO Eteplirsen became the first and only FDA-approved therapy to treat the underlying genetic cause of Duchenne muscular dystrophy (DMD) by skipping exon 51 of the dystrophin gene. Although PMO therapies such as Eteplirsen show significant promise, the dosages required are often multiple grams per week due to limited intracellular delivery. Creating conjugates between CPPs and PMOs has been one effective approach in improving delivery. O'Donovan el al. have looked at a modest library of sixteen different CPP-PMO conjugates and Moulton et al. have identified arginine-rich peptides that have improved the delivery of PMO cargoes for DMD. However, there has yet to be a systematic investigation of the features of CPPs that promote PMO delivery.

Provided herein are peptide-oligonucleotide-conjugates comprising an oligonucleotide covalently bound to a cell-penetrating peptide. Also provided herein are methods of treating a disease in a subject in need thereof, comprising administering to the subject a peptide-oligonucleotide-conjugate described herein. The oligonucleotides, and thereby the peptide-oligonucleotide-conjugates, described herein display stronger affinity for DNA and RNA without compromising sequence selectivity, relative to native or unmodified oligonucleotides. In some embodiments, the oligonucleotides of the disclosure minimize or prevent cleavage by RNase H. In some embodiments, the antisense oligonucleotides of the disclosure do not activate RNase H.

The peptides described herein impart to their corresponding peptide-oligonucleotide-conjugates lower toxicity, enhance the activity of the oligonucleotide, improve pharmacokinetics and tissue distribution, improve cellular delivery, and impart both reliable and controllable in vivo distribution.

Definitions

Listed below are definitions of various terms used to describe this disclosure. These definitions apply to the terms as they are used throughout this specification and claims, unless otherwise limited in specific instances, either individually or as part of a larger group.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH₂—CH₂—CH₃, —CH₂—CH₂—CH₂—OH, —CH₂—CH₂—NH—CH₃, —CH₂—S—CH₂—CH₃, and —CH₂—CH₂—S(=O)—CH₃. Up to two heteroatoms may be consecutive, such as, for example, —CH₂—NH—OCH₃, or —CH₂—CH₂—S—S—CH₃.

The term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. In various embodiments, examples of an aryl group may include phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_{6-12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_{1-9}$-heteroaryl indicates the number of carbon atoms contained in the heteroaryl group without including the number of heteroatoms. For example, a $C_{1-9}$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

The term "protecting group" or "chemical protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, monomethoxytrityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while coexisting amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

The term "nucleobase," "base pairing moiety," "nucleobase-pairing moiety," or "base" refers to the heterocyclic ring portion of a nucleoside, nucleotide, and/or morpholino subunit. Nucleobases may be naturally occurring, or may be modified or analogs of these naturally occurring nucleobases, e.g., one or more nitrogen atoms of the nucleobase may be independently at each occurrence replaced by carbon. Exemplary analogs include hypoxanthine (the base component of the nucleoside inosine); 2, 6-diaminopurine; 5-methyl cytosine; C5-propynyl-modified pyrimidines; 10-(9-(aminoethoxy)phenoxazinyl) (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glen-research.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

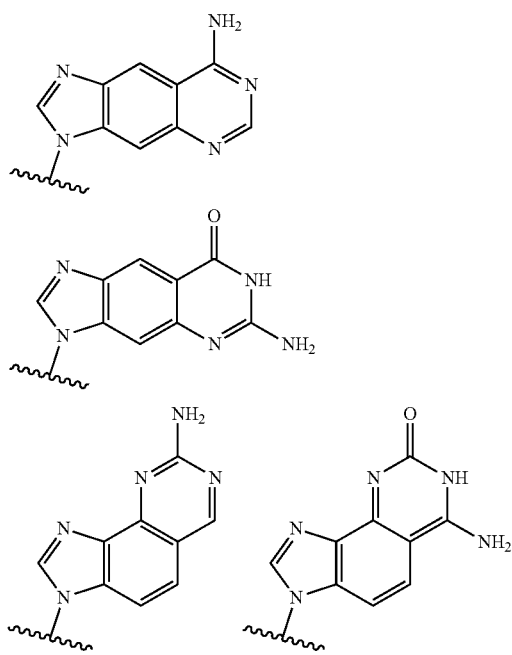

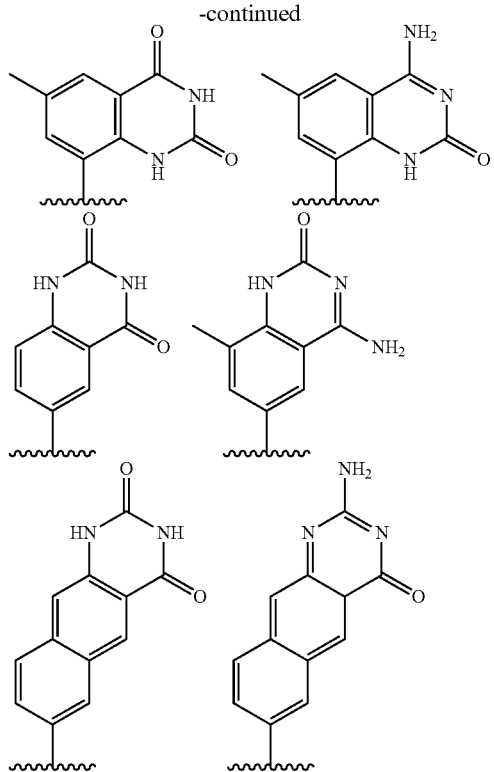

The terms "oligonucleotide" or "oligomer" refer to a compound comprising a plurality of linked nucleosides, nucleotides, or a combination of both nucleosides and nucleotides. In specific embodiments provided herein, an oligonucleotide is a morpholino oligonucleotide.

The phrase "morpholino oligonucleotide" or "PMO" refers to a modified oligonucleotide having morpholino subunits linked together by phosphoramidate or phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The terms "antisense oligomer," "antisense compound" and "antisense oligonucleotide" are used interchangeably and refer to a sequence of subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The oligomer may have exact (perfect) or near (sufficient) sequence complementarity to the target sequence; variations in sequence near the termini of an oligomer are generally preferable to variations in the interior.

Such an antisense oligomer can be designed to block or inhibit translation of mRNA or to inhibit/alter natural or abnormal pre-mRNA splice processing, and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. In various embodiments, a target sequence may be any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The antisense oligonucleotide and the target RNA are complementary to each other when a sufficient number of corresponding positions in each molecule are occupied by nucleotides which can hydrogen bond with each other, such that stable and specific binding occurs between the oligonucleotide and the target. Thus, "specifically hybridizable" and "complementary" are terms which are used to indicate a sufficient degree of complementarity or precise pairing such that stable and specific binding occurs between the oligonucleotide and the target. It is understood in the art that the sequence of an oligonucleotide need not be 100% complementary to that of its target sequence to be specifically hybridizable. An oligonucleotide is specifically hybridizable when binding of the oligonucleotide to the target molecule interferes with the normal function of the target RNA, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases. In some embodiments, the nucleobase is covalently linked at the N9 atom of the purine base, or at the N1 atom of the pyrimidine base, to the morpholine ring of a nucleotide or nucleoside.

Purine bases comprise a pyrimidine ring fused to an imidazole ring, as described by the general formula:

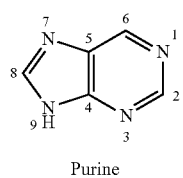

Purine

Adenine and guanine are the two purine nucleobases most commonly found in nucleic acids. These may be substituted with other naturally-occurring purines, including but not limited to N6-methyladenine, N2-methylguanine, hypoxanthine, and 7-methylguanine.

Pyrimidine bases comprise a six-membered pyrimidine ring as described by the general formula:

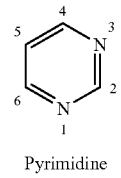

Pyrimidine

Cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; N2-cyclopentylguanine (cPent-G), N2-cyclopentyl-2-aminopurine (cPent-AP), and N2-propyl-2-aminopurine (Pr-AP), pseudouracil or derivatives thereof, and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Pseudouracil is a naturally occurring isomerized version of uracil, with a C-glycoside rather than the regular N-glycoside as in uridine.

Certain modified or substituted nucleobases are particularly useful for increasing the binding affinity of the antisense oligonucleotides of the disclosure. These include 5-substituted pyrimidines, 6-azapyrimidines and N-2, N-6 and 0-6 substituted purines, including 2-aminopropyladenine, 5-propynyluracil and 5-propynylcytosine. In various embodiments, nucleobases may include 5-methylcytosine substitutions, which have been shown to increase nucleic acid duplex stability by 0.6-1.2° C.

In some embodiments, modified or substituted nucleobases are useful for facilitating purification of antisense oligonucleotides. For example, in certain embodiments, antisense oligonucleotides may contain three or more (e.g., 3, 4, 5, 6 or more) consecutive guanine bases. In certain antisense oligonucleotides, a string of three or more consecutive guanine bases can result in aggregation of the oligonucleotides, complicating purification. In such antisense oligonucleotides, one or more of the consecutive guanines can be substituted with hypoxanthine. The substitution of hypoxanthine for one or more guanines in a string of three or more consecutive guanine bases can reduce aggregation of the antisense oligonucleotide, thereby facilitating purification.

The oligonucleotides provided herein are synthesised and do not include antisense compositions of biological origin. The molecules of the disclosure may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution, or absorption, or a combination thereof.

The terms "complementary" and "complementarity" refer to oligonucleotides (i.e., a sequence of nucleotides) related by base-pairing rules. For example, the sequence "T-G-A (5-3')," is complementary to the sequence "T-C-A (5'-3')." Complementarity may be "partial," in which only some of the nucleic acids' bases are matched according to base pairing rules. Or, there may be "complete," "total," or "perfect" (100%) complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100% complementarity. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5'-terminus, 3'-terminus, or both termini.

The term "peptide" refers to a compound comprising a plurality of linked amino acids. The peptides provided herein can be considered to be cell penetrating peptides.

The terms "cell penetrating peptide" and "CPP" are used interchangeably and refer to cationic cell penetrating peptides, also called transport peptides, carrier peptides, or peptide transduction domains. The peptides, provided herein, have the capability of inducing cell penetration within 100% of cells of a given cell culture population and allow macromolecular translocation within multiple tissues in vivo upon systemic administration. In various embodiments, a CPP embodiment of the disclosure may include an arginine-rich peptide as described further below.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

As used herein, "pharmaceutically acceptable salts" refers to derivatives of the disclosed oligonucleotides wherein the parent oligonucleotide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Peptide-Oligonucleotide-Conjugates

Provided herein are oligonucleotides chemically linked to a cell-penetrating peptide. The cell-penetrating peptide enhances activity, cellular distribution, or cellular uptake of the oligonucleotide. In particular, the cell-penetrating peptide is a linear, or non-cyclic, peptide. In some embodiments, the CPP can be an arginine-rich peptide. The oligonucleotides can additionally be chemically-linked to one or more heteroalkyl moieties (e.g., polyethylene glycol) that further enhance the activity, cellular distribution, or cellular uptake of the oligonucleotide. In one exemplary embodiment, the polypeptide, e.g., the arginine-rich polypeptide, is covalently coupled at its N-terminal or C-terminal residue to either end, or both ends, of the oligonucleotide.

Thus, in one aspect, provided herein is a peptide-oligonucleotide-conjugate of Formula I:

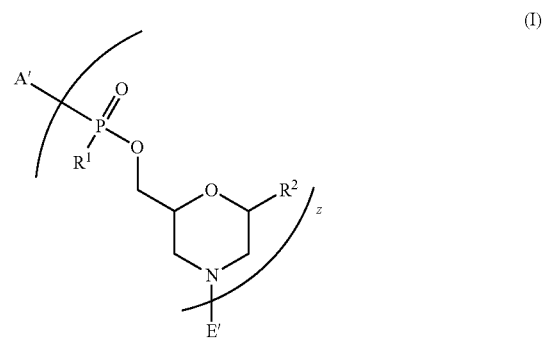

(I)

or a pharmaceutically acceptable salt thereof,
wherein:
A' is selected from —NHCH$_2$C(O)NH$_2$, —N(C$_{1-6}$-alkyl)CH$_2$C(O)NH$_2$,

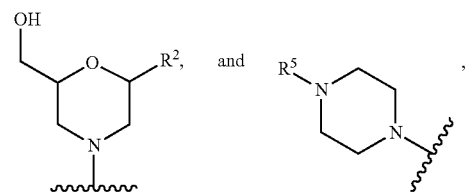

wherein
R$^5$ is —C(O)(O-alkyl)$_x$-OH, wherein x is 3-10 and each alkyl group is, independently at each occurrence, C$_{2-6}$-alkyl, or R$^5$ is selected from —C(O)C$_{1-6}$-alkyl, trityl, monomethoxytrityl, —(C$_{1-6}$-alkyl)R$^6$, —(C$_{1-6}$-heteroalkyl)-R$^6$, aryl-R$^6$, heteroaryl-R$^6$, —C(O)O—(C$_{1-6}$-alkyl)-R$_6$, —C(O)O-aryl-R$^6$, —C(O)O-heteroaryl-R$^6$, and

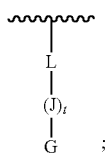

wherein $R^6$ is selected from OH, SH, and $NH_2$, or $R^6$ is O, S, or NH, covalently linked to a solid support;

each $R^1$ is independently selected from OH and $-NR^3R^4$, wherein each $R^3$ and $R^4$ are, independently at each occurrence, $-C_{1-6}$-alkyl;

each $R^2$ is independently selected from H, a nucleobase, and a nucleobase functionalized with a chemical protecting-group, wherein the nucleobase, independently at each occurrence, comprises a $C_{3-6}$-heterocyclic ring selected from pyridine, pyrimidine, triazinane, purine, and deaza-purine;

z is 8-40; and

E' is selected from H, $-C_{1-6}$-alkyl, $-C(O)C_{1-6}$-alkyl, benzoyl, stearoyl, trityl, monomethoxytrityl, dimethoxytrityl, trimethoxytrityl,

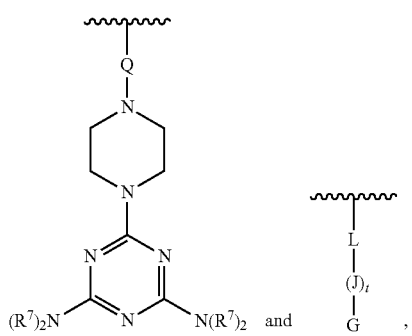

wherein

Q is $-C(O)(CH_2)_6C(O)-$ or $-C(O)(CH_2)_2S_2(CH_2)_2C(O)-$, and $R^7$ is $-(CH_2)_2OC(O)N(R^8)_2$, wherein $R^8$ is $-(CH_2)_6NHC(=NH)NH_2$, and wherein L is covalently linked by an amide bond to the amino-terminus of J, and L is $-C(O)(CH_2)_{1-6}-C_{1-6}$-heteroaromatic-$(CH_2)_{1-6}C(O)$;

t is 5-27;

each J is, independently at each occurrence, selected from the group consisting of arginine, glycine, leucine, alanine, phenylalanine, methionine, tryptophan, lysine, glutamine, glutamic acid, serine, proline, valine, isoleucine, cysteine, tyrosine, histidine, asparagine, aspartic acid, and threonine;

wherein at least one J is arginine;

G is covalently linked by an amide bond to the carboxy-terminus of J, and G is selected from H, $-C(O)C_{1-6}$-alkyl, benzoyl, and stearoyl; and wherein at least one of the following conditions is true:

1) A' is

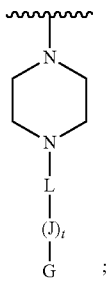

or 2) E' is

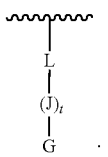

In one embodiment, E' is selected from H, $-C_{1-6}$-alkyl, $-C(O)C_{1-6}$-alkyl, benzoyl, stearoyl, trityl, monomethoxytrityl, dimethoxytrityl, trimethoxytrityl, and

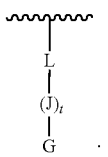

In yet another embodiment, A' is selected from $-N(C_{1-6}\text{-alkyl})CH_2C(O)NH_2$.

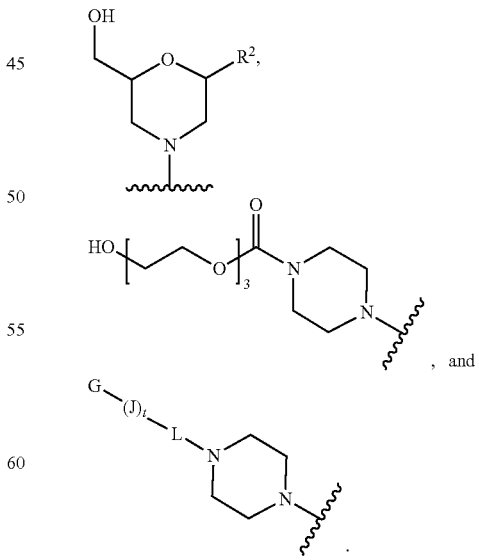

In another embodiment E' is selected from H, $-C(O)CH_3$, benzoyl, stearoyl, trityl, 4-methoxytrityl, and

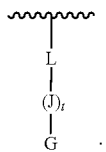

In still another embodiment, A' is selected from —N(C$_{1-6}$-alkyl)CH$_2$C(O)NH$_2$,

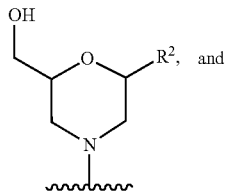, and

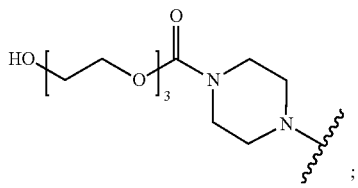

and
E' is

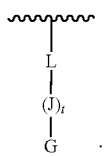

In yet another embodiment, A' is

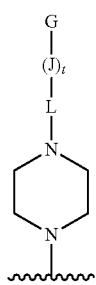

In another embodiment, E' is selected from H, —C(O)CH$_3$, trityl, 4-methoxytrityl, benzoyl, and stearoyl.

In yet another embodiment, E' is selected from H and —C(O)CH$_3$.

In still another embodiment, the peptide-oligonucleotide-conjugate of Formula I is a peptide-oligonucleotide-conjugate of Formula Ia:

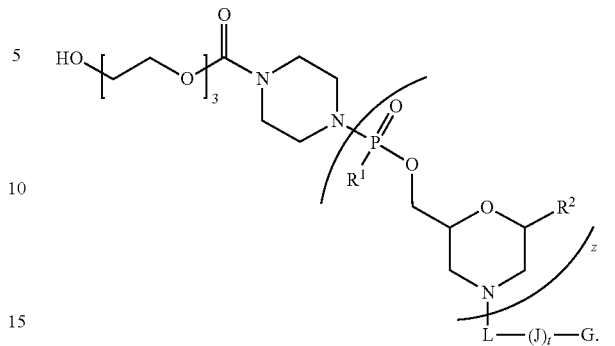

(Ia)

In another embodiment, the peptide-oligonucleotide-conjugate of Formula I is a peptide-oligonucleotide-conjugate of Formula Ib:

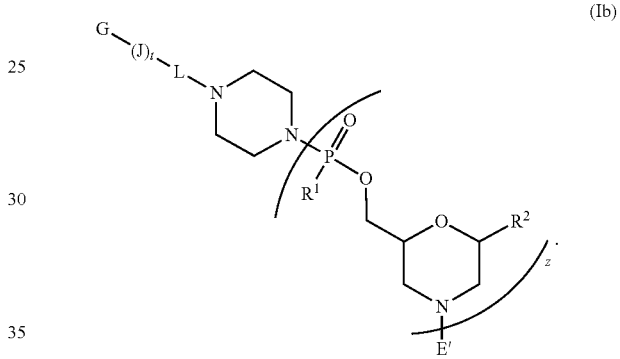

(Ib)

In an embodiment of Formula I and Ib, E' is selected from H, C$_{1-6}$ alkyl, —C(O)CH$_3$, benzoyl, and stearoyl.

In another embodiment of Formula I and Ib, E' is selected from H and —C(O)CH$_3$.

In an embodiment of Formula I, Ia, and Ib, each J is independently selected from glycine, alanine, leucine, methionine, phenylalanine, tryptophan, lysine, glutamine, glutamic acid, serine, proline, valine, arginine, and threonine.

In another embodiment of Formula I, Ia, and Ib, each J is independently selected from arginine, lysine, and glutamine.

In another embodiment of Formula I, Ia, and Ib, each J is independently selected from glycine, leucine, alanine, phenylalanine, serine, threonine, methionine, tryptophan, glutamine, proline, lysine, arginine, and valine.

In another embodiment of Formula I, Ia, and Ib, each J is independently selected from arginine, isoleucine, proline, leucine, phenylalanine, and glycine.

In still another embodiment of Formula I, Ia, and Ib, each J is independently selected from glycine, arginine, proline, glutamic acid, serine, lysine, and leucine.

In yet another embodiment of Formula I, Ia, and Ib, each J is independently selected from alanine, leucine, tryptophan, lysine, threonine, valine, proline, and arginine.

In still another embodiment of Formula I, Ia, and Ib, each R' is N(CH$_3$)$_2$.

In yet another embodiment of Formula I, Ia, and Ib, each R$^2$ is a nucleobase, wherein the nucleobase independently at each occurrence comprises a C$_{4-6}$-heterocyclic ring selected from pyridine, pyrimidine, triazinane, purine, and deazapurine.

In another embodiment of Formula I, Ia, and Ib, each $R^2$ is a nucleobase, wherein the nucleobase independently at each occurrence comprises a $C_{4-6}$-heterocyclic ring selected from pyrimidine, purine, and deaza-purine.

In still another embodiment of Formula I, Ia, and Ib, each $R^2$ is a nucleobase independently at each occurrence selected from adenine, 2,6-diaminopurine, 7-deaza-adenine, guanine, 7-deaza-guanine, hypoxanthine, cytosine, 5-methyl-cytosine, thymine, uracil, and hypoxanthine.

In yet another embodiment of Formula I, Ia, and Ib, each $R^2$ is a nucleobase independently at each occurrence selected from adenine, guanine, cytosine, 5-methyl-cytosine, thymine, uracil, and hypoxanthine.

In another embodiment of Formula I, Ia, and Ib, L is —C(O)(CH$_2$)$_{1-6}$-triazole-(CH$_2$)$_{1-6}$C(O)—.

In another embodiment of Formula I, Ia, and Ib, L is

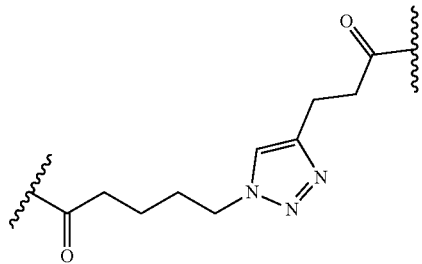 [SMILES: *C(=O)CCCCn1cc(CCC(*)=O)nn1]

In another embodiment of Formula I, Ia, and Ib, G is selected from H, C(O)CH$_3$, benzoyl, and stearoyl.

In still another embodiment of Formula I, Ia, and Ib, G is H or —C(O)CH$_3$.

In yet another embodiment of Formula I, Ia, and Ib, G is H.

In yet another embodiment of Formula I, Ia, and Ib, G is —C(O)CH$_3$.

In another embodiment of Formula I, Ia, and Ib, J is RRRRRRRRRRRR (SEQ ID NO.: 1), GLAFLGFL-GAAGSTMGAWSQPKKKRKV (SEQ ID NO.: 2), RRIR-PRPPRLPRPRPRPLPFPRPG (SEQ ID NO.: 3), RKKRRQRRR (SEQ ID NO.: 4), RRRRRRRRRR (SEQ ID NO.: 5), GRPRESGKKRKRKRLKP (SEQ ID NO.: 6), ALWKTLLKKVLKAPKKKRKV (SEQ ID NO.: 7), RRIPNRRPRR (SEQ ID NO.: 8), TRRQRTRRARRNR (SEQ ID NO.: 9), HARIKPTFRRLKWKYKGKFW (SEQ ID NO.: 10), GIGAVLKVLTTGLPALISWIKRKRQQ (SEQ ID NO.: 11), LRRERQSRLRRERQSR (SEQ ID NO.: 12), RRRRRRRR (SEQ ID NO.: 13), RQIKIWFQNRRMKWKK (SEQ ID NO.: 14), KRARN-TEAARRSRARKLQRMKQ (SEQ ID NO.: 15), RHIKIWFQNRRMKWKK (SEQ ID NO.: 16), RRRRRRRR (SEQ ID NO.: 17), KMTRAQR-RAAARRNRWTAR (SEQ ID NO.: 18), RGGRLSYS-RRRFSTSTGR (SEQ ID NO.: 19), KQINNW-FINQRKRHWK (SEQ ID NO.: 20), KLWMRWYSPTTRRYG (SEQ ID NO.: 21), RRWWRRWRR (SEQ ID NO.: 22), SQIKIWFQNKRAK-IKK (SEQ ID NO.: 23), GAYDLRRRERQSRLRRRER-QSR (SEQ ID NO.: 24), TRRNKRNRIQEQLNRK (SEQ ID NO.: 25), GKRKKKGKLGKKRDP (SEQ ID NO.: 26), RQVTIWFQNRRVKEKK (SEQ ID NO.: 27), RLRWR (SEQ ID NO.: 28), PPRPPRPPRPPRPPR (SEQ ID NO.: 29), CAYHRLRRC (SEQ ID NO.: 30), SRRARR-SPRHLGSG (SEQ ID NO.: 31), PPRPPRPPRPPR (SEQ ID NO.: 32), NAKTRRHERRRKLAIER (SEQ ID NO.: 33), VKRGLKLRHVRPRVTRMDV (SEQ ID NO.: 34), LYKKGPAKKGRPPLRGWFH (SEQ ID NO.: 35), TAKTRYKARRAELIAERR (SEQ ID NO.: 36), KGTYKKKLMRIPLKGT (SEQ ID NO.: 37), PPRPPRPPR (SEQ ID NO.: 38), RASKRDGSWVKKLHRILE (SEQ ID NO.: 39), TRSSRAGLQWPVGRVHRLLRK (SEQ ID NO.: 40), FKIYDKKVRTRVVKH (SEQ ID NO.: 41), VRLPPPVRLPPPVRLPPP (SEQ ID NO.: 42), GPFHFYQFLFPPV (SEQ ID NO.: 43), PLILLRLLRGQF (SEQ ID NO.: 44), YTAIAWVKAFIRKLRK (SEQ ID NO.: 45), KETWWETWWTEWSQPKKRKV (SEQ ID NO.: 46), LIRLWSHLIHIWFQNRRLKWKKK (SEQ ID NO.: 47), VDKGSYLPRPTPPRPIYNRN (SEQ ID NO.: 48), MDAQTRRERAEKQAQWKAAN (SEQ ID NO.: 49), GSPWGLQHHPPRT (SEQ ID NO.: 50), KLALKALKAL-KAALKLA (SEQ ID NO.: 51), IPALK (SEQ ID NO.: 52), VPALR (SEQ ID NO.: 53), LLIILRRRIRKQAHAHSK (SEQ ID NO.: 54), IAWVKAFIRKLRKGPLG (SEQ ID NO.: 55), AAVLLPVLLAAPVQRKRQKLP (SEQ ID NO.: 56), TSPLNIHNGQKL (SEQ ID NO.: 57), VPTLK (SEQ ID NO.: 58), or VSALK (SEQ ID NO.: 59).

In still another embodiment of Formula I, Ia, and Ib, J is RRRRRRRRRRRR (SEQ ID NO.: 1), GLAFLGFL-GAAGSTMGAWSQPKKKRKV (SEQ ID NO.: 2), RRIR-PRPPRLPRPRPRPLPFPRPG (SEQ ID NO.: 3), RKKRRQRRR (SEQ ID NO.: 4), RRRRRRRRRR (SEQ ID NO.: 5), GRPRESGKKRKRKRLKP (SEQ ID NO.: 6), ALWKTLLKKVLKAPKKKRKV (SEQ ID NO.: 7), RRIPNRRPRR (SEQ ID NO.: 8), TRRQRTRRARRNR (SEQ ID NO.: 9), HARIKPTFRRLKWKYKGKFW (SEQ ID NO.: 10), GIGAVLKVLTTGLPALISWIKRKRQQ (SEQ ID NO.: 11), LRRERQSRLRRERQSR (SEQ ID NO.: 12), RRRRRRRR (SEQ ID NO.: 13), RQIKIWFQNRRMKWKK (SEQ ID NO.: 14), KRARN-TEAARRSRARKLQRMKQ (SEQ ID NO.: 15), RHIKIWFQNRRMKWKK (SEQ ID NO.: 16), RRRRRRRR (SEQ ID NO.: 17), KMTRAQR-RAAARRNRWTAR (SEQ ID NO.: 18), RGGRLSYS-RRRFSTSTGR (SEQ ID NO.: 19), KQINNW-FINQRKRHWK (SEQ ID NO.: 20), KLWMRWYSPTTRRYG (SEQ ID NO.: 21), RRWWRRWRR (SEQ ID NO.: 22), SQIKIWFQNKRAK-IKK (SEQ ID NO.: 23), GAYDLRRRERQSRLRRRER-QSR (SEQ ID NO.: 24), TRRNKRNRIQEQLNRK (SEQ ID NO.: 25), GKRKKKGKLGKKRDP (SEQ ID NO.: 26), RQVTIWFQNRRVKEKK (SEQ ID NO.: 27), RLRWR (SEQ ID NO.: 28), PPRPPRPPRPPRPPR (SEQ ID NO.: 29), CAYHRLRRC (SEQ ID NO.: 30), SRRARR-SPRHLGSG (SEQ ID NO.: 31), PPRPPRPPRPPR (SEQ ID NO.: 32), NAKTRRHERRRKLAIER (SEQ ID NO.: 33), VKRGLKLRHVRPRVTRMDV (SEQ ID NO.: 34), LYKKGPAKKGRPPLRGWFH (SEQ ID NO.: 35), TAKTRYKARRAELIAERR (SEQ ID NO.: 36), or KGTYKKKLMRIPLKGT (SEQ ID NO.: 37).

In yet another embodiment of Formula I, Ia, and Ib, J is RRRRRRRRRRRR (SEQ ID NO.: 1), GLAFLGFL-GAAGSTMGAWSQPKKKRKV (SEQ ID NO.: 2), RRIR-PRPPRLPRPRPRPLPFPRPG (SEQ ID NO.: 3), RKKRRQRRR (SEQ ID NO.: 4), RRRRRRRRRR (SEQ ID NO.: 5), GRPRESGKKRKRKRLKP (SEQ ID NO.: 6), or ALWKTLLKKVLKAPKKKRKV (SEQ ID NO.: 7).

In yet another embodiment of Formula I, Ia, and Ib, the oligonucleotide-peptide conjugate demonstrates at least a two-fold improvement in uptake as compared to unconjugated oligonucleotide.

In an embodiment, the oligonucleotide-peptide conjugate demonstrates at least a five-fold improvement in uptake as compared to unconjugated oligonucleotide.

In another embodiment, the oligonucleotide-peptide conjugate demonstrates improvement in uptake as compared to the corresponding Cy5.5-peptide conjugate.

In yet another embodiment, the oligonucleotide comprises a targeting sequence having sequence complementarity to an RNA target. In a specific embodiment, the RNA target is a cellular RNA target. In another specific embodiment, the targeting sequence has sufficient sequence complementarity to bind to the RNA target. In yet another specific embodiment, the targeting sequence has perfect sequence complementarity to the RNA target.

Representative peptide-oligonucleotide-conjugates of the disclosure include, amongst others, peptide-oligonucleotide-conjugates of the following structure:

RRWWRRWRR (SEQ ID NO.: 22), SQIKIWFQNKRAKIKK (SEQ ID NO.: 23), GAYDLRRRERQSRLRRRERQSR (SEQ ID NO.: 24), TRRNKRNRIQEQLNRK (SEQ ID NO.: 25), GKRKKKGKLGKKRDP (SEQ ID NO.: 26), RQVTIWFQNRRVKEKK (SEQ ID NO.: 27), RLRWR (SEQ ID NO.: 28), PPRPPRPPRPPRPPR (SEQ ID NO.: 29), CAYHRLRRC (SEQ ID NO.: 30), SRRARRSPRHLGSG (SEQ ID NO.: 31), PPRPPRPPRPPR (SEQ ID NO.: 32), NAKTRRHERRRKLAIER (SEQ ID NO.: 33), VKRGLKLRHVRPRVTRMDV (SEQ ID NO.: 34), LYKKGPAKKGRPPLRGWFH (SEQ ID NO.: 35), TAKTRYKARRAELIAERR (SEQ ID NO.: 36), KGTYKKKLMRIPLKGT (SEQ ID NO.: 37), PPRPPRPPR (SEQ ID NO.: 38), RASKRDGSWVKKLHRILE (SEQ ID NO.: 39), TRSSRAGLQWPVGRVHRLLRK (SEQ ID NO.: 40),

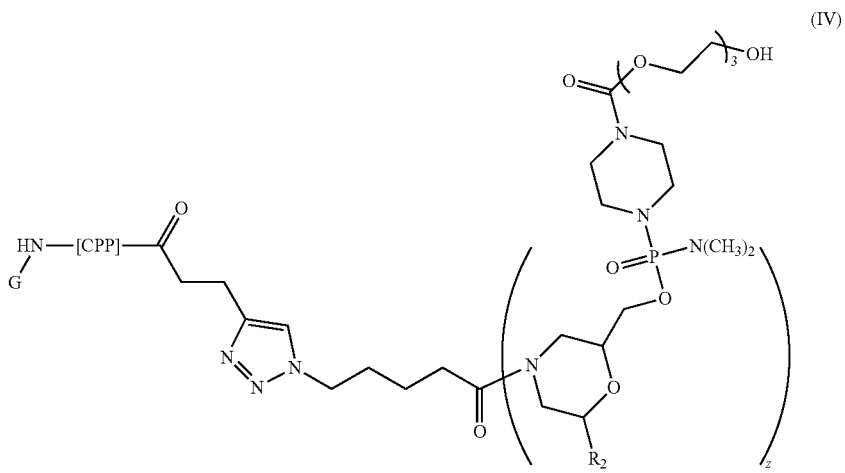

(IV)

or a pharmaceutically acceptable salt thereof, wherein
G is H or —C(O)CH$_3$, wherein G is covalently linked by an amide bond to the carboxy terminus of the peptide;
R$^2$ is a nucleobase, independently at each occurrence, selected from adenine, guanine, cytosine, 5-methyl-cytosine, thymine, uracil, and hypoxanthine;
z is 8-40; and
CPP is, independently at each occurrence, selected from
RRRRRRRRRRRR (SEQ ID NO.: 1), GLAFLGFLGAAGSTMGAWSQPKKKRKV (SEQ ID NO.: 2), RRIRPRPPRLPRPRPRPLPFPRPG (SEQ ID NO.: 3), RKKRRQRRR (SEQ ID NO.: 4), RRRRRRRRR (SEQ ID NO.: 5), GRPRESGKKRKRKRLKP (SEQ ID NO.: 6), ALWKTLLKKVLKAPKKKRKV (SEQ ID NO.: 7), RRIPNRRPRR (SEQ ID NO.: 8), TRRQRTRRARRNR (SEQ ID NO.: 9), HARIKPTFRRLKWKYKGKFW (SEQ ID NO.: 10), GIGAVLKVLTTGLPALISWIKRKRQQ (SEQ ID NO.: 11), LRRERQSRLRRERQSR (SEQ ID NO.: 12), RRRRRRRR (SEQ ID NO.: 13), RQIKIWFQNRRMKWKK (SEQ ID NO.: 14), KRARNTEAARRSRARKLQRMKQ (SEQ ID NO.: 15), RHIKIWFQNRRMKWKK (SEQ ID NO.: 16), RRRRRRRR (SEQ ID NO.: 17), KMTRAQRRAAARRNRWTAR (SEQ ID NO.: 18), RGGRLSYSRRRFSTSTGR (SEQ ID NO.: 19), KQINNWFINQRKRHWK (SEQ ID NO.: 20), KLWMRWYSPTTRRYG (SEQ ID NO.: 21), FKIYDKKVRTRVVKH (SEQ ID NO.: 41), VRLPPPVRLPPPVRLPPP (SEQ ID NO.: 42), GPFHFYQFLFPPV (SEQ ID NO.: 43), PLILLRLLRGQF (SEQ ID NO.: 44), YTAIAWVKAFIRKLRK (SEQ ID NO.: 45), KETWWETWWTEWSQPKKRKV (SEQ ID NO.: 46), LIRLWSHLIHIWFQNRRLKWKKK (SEQ ID NO.: 47), VDKGSYLPRPTPPRPIYNRN (SEQ ID NO.: 48), MDAQTRRRERRAEKQAQWKAAN (SEQ ID NO.: 49), GSPWGLQHHPPRT (SEQ ID NO.: 50), KLALKALKALKAALKLA (SEQ ID NO.: 51), IPALK (SEQ ID NO.: 52), VPALR (SEQ ID NO.: 53), LLIILRRRIRKQAHAHSK (SEQ ID NO.: 54), IAWVKAFIRKLRKGPLG (SEQ ID NO.: 55), AAVLLPVLLAAPVQRKRQKLP (SEQ ID NO.: 56), TSPLNIHNGQKL (SEQ ID NO.: 57), VPTLK (SEQ ID NO.: 58), or VSALK (SEQ ID NO.: 59).

In one embodiment of the peptide-oligonucleotide-conjugates of the disclosure, G is H.

In another embodiment of the peptide-oligonucleotide-conjugates of the disclosure, G is —C(O)CH$_3$.

In an embodiment, L is covalently linked to the carboxy terminus of the peptide, and G is covalently linked to the amino terminus of the peptide.

As used herein, "G is covalently linked by an amide bond to the carboxy-terminus of J," indicates that the carboxy-terminus of J (—COOH) is covalently bound to variable G via an N(H) group, wherein the hydroxyl group of the carboxy-terminus of J is replaced with N(H). For example, when G is H, the following structure is formed by J and G:

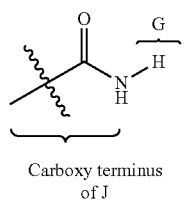

Carboxy terminus of J

In some embodiments, the peptide-oligonucleotide-conjugates described herein are unsolvated. In other embodiments, one or more of the peptide-oligonucleotide-conjugates are in solvated form. As known in the art, the solvate can be any of pharmaceutically acceptable solvent, such as water, ethanol, and the like.

Although the peptide-oligonucleotide-conjugates of Formulae I, Ia, Ib, and II are depicted in their neutral forms, in some embodiments, these peptide-oligonucleotide-conjugates are used in a pharmaceutically acceptable salt form.

Oligonucleotides

Important properties of morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA, $T_M$ values above about 45° C. in relatively short oligonucleotides (e.g., 10-15 bases); 3) the ability of the oligonucleotide to be actively or passively transported into mammalian cells; and 4) the ability of the oligonucleotide and oligonucleotide:RNA heteroduplex to resist RNAse and RNase H degradation, respectively.

The stability of the duplex formed between an oligomer and a target sequence is a function of the binding $T_M$ and the susceptibility of the duplex to cellular enzymatic cleavage. The $T_M$ of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding $T_M$, with respect to a complementary-sequence RNA, of greater than body temperature and, in some embodiments greater than about 45° C. or 50° C. $T_M$'s in the range 60-80° C. or greater are also included. According to well-known principles, the $T_M$ of an oligomer, with respect to a complementary-based RNA hybrid, can be increased by increasing the ratio of C:G paired bases in the duplex, or by increasing the length (in base pairs) of the heteroduplex, or both. At the same time, for purposes of optimizing cellular uptake, it may be advantageous to limit the size of the oligomer. For this reason, compounds of the disclosure include compounds that show a high $T_M$ (45-50° C. or greater) at a length of 25 bases or less.

The length of an oligonucleotide may vary so long as it is capable of binding selectively to the intended location within the pre-mRNA molecule. The length of such sequences can be determined in accordance with selection procedures described herein. Generally, the oligonucleotide will be from about 8 nucleotides in length up to about 50 nucleotides in length. For example, the length of the oligonucleotide (z) can be 8-38, 8-25, 15-25, 17-21, or about 18. It will be appreciated however that any length of nucleotides within this range may be used in the methods described herein.

In some embodiments, the antisense oligonucleotides contain base modifications or substitutions. For example, certain nucleo-bases may be selected to increase the binding affinity of the antisense oligonucleotides described herein. These include 5-substituted pyrimidines, 6-azapyrimidines and N-2, N-6 and 0-6 substituted purines, including 2-aminopropyladenine, 5-propynyluracil, 5-propynylcytosine and 2,6-diaminopurine. 5-methylcytosine substitutions have been shown to increase nucleic acid duplex stability by 0.6-1.2° C., and may be incorporated into the antisense oligonucleotides described herein. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligonucleotide comprises an N-2, N-6 substituted purine base. In one embodiment, the N-2, N-6 substituted purine base is 2,6-diaminopurine.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Accordingly, in one aspect, provided herein is an oligonucleotide of Formula II:

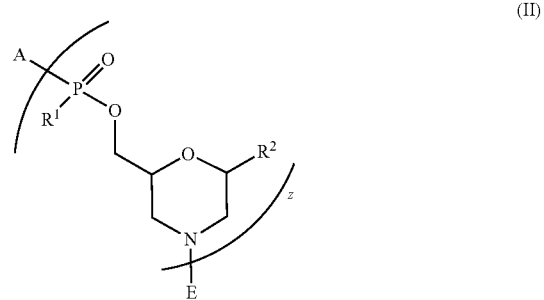

or a pharmaceutically acceptable salt thereof,
wherein
A is selected from the group consisting of OH, —NHCH$_2$C(O)NH$_2$, —N(C$_{1-6}$-alkyl)CH$_2$C(O)NH$_2$,

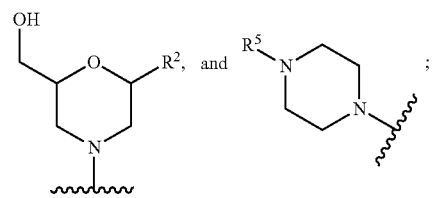

$R^5$ is —C(O)(O-alkyl)$_x$OH, wherein x is 3-10 and each alkyl group is independently at each occurrence —C$_2$-

6-alkyl, or $R^5$ is selected from the group consisting of —C(O)$C_{1-6}$-alkyl, trityl, monomethoxytrityl, —$C_{1-6}$-alkyl-$R^6$, —$C_{1-6}$-heteroalkyl-$R^6$, -aryl-$R^6$, -heteroaryl-$R^6$, —C(O)O—$C_{1-6}$-alkyl-$R^6$, —C(O)O-aryl-$R^6$, and —C(O)O-heteroaryl-$R^6$;

$R^6$ is selected from the group consisting of OH, SH, and $NH_2$, or $R^6$ is O, S, or NH, covalently linked to a solid support;

each $R^1$ is independently OH or —$NR^3R^4$;

each $R^3$ and $R^4$ are independently at each occurrence —$C_{1-6}$-alkyl;

each $R^2$ is independently selected from the group consisting of H, a nucleobase, and a nucleobase functionalized with a chemical protecting-group, wherein the nucleobase independently at each occurrence comprises a $C_{3-6}$-heterocyclic ring selected from the group consisting of pyridine, pyrimidine, triazinane, purine, and deaza-purine;

z is 8-40;

E is selected from the group consisting of H, —$C_{1-6}$-alkyl, —C(O)$C_{1-6}$-alkyl, benzoyl, stearoyl, trityl, monomethoxytrityl, dimethoxytrityl, trimethoxytrityl, and

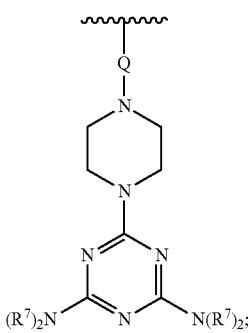

Q is —C(O)($CH_2$)$_6$C(O)— or —C(O)($CH_2$)$_2S_2$($CH_2$)$_2$C(O)—;

$R^7$ is —($CH_2$)$_2$OC(O)N($R^8$)$_2$;

$R^8$ is —($CH_2$)NHC(=NH)$NH_2$.

In one embodiment of Formula II, A is

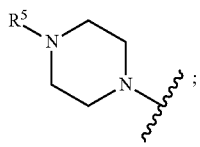

E is selected from the group consisting of H, —C(O)$CH_3$, benzoyl, and stearoyl;

$R^5$ is —C(O)(O-alkyl)$_x$-OH, wherein each alkyl group is independently at each occurrence —$C_{2-6}$-alkyl, trityl, and 4-methoxytrityl; and each $R^2$ is independently a nucleobase, wherein the nucleobase independently at each occurrence comprises a $C_{4-6}$-heterocyclic ring selected from the group consisting of pyridine, pyrimidine, purine, and deaza-purine.

In another embodiment of Formula II, $R^5$ is C(O)(O—$CH_2CH_2$)$_3$—OH; and each $R^2$ is independently a nucleobase, wherein the nucleobase independently at each occurrence comprises a pyrimidine or a purine.

In still another embodiment, the oligonucleotide of Formula II is an oligonucleotide of Formula IIa:

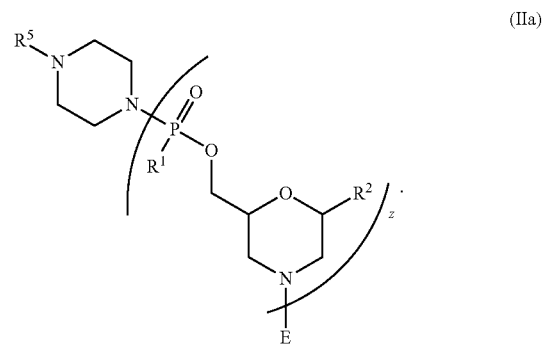

(IIa)

In an embodiment of Formula II and IIa, $R^2$ is independently at each occurrence adenine, 2,6-diaminopurine, guanine, hypoxanthine, cytosine, 5-methyl-cytosine, thymine, uracil, and hypoxanthine; and each $R^1$ is —N($CH_3$)$_2$.

Provided in Table 1 are various embodiments of nucleotide moieties as described herein.

TABLE 1

Various embodiments of nucleotide moieties.

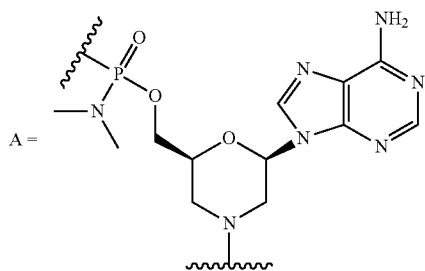 [SMILES: *N1C[C@@H](COP(*)(=O)N(C)C)O[C@@H](n2cnc3c(N)ncnc32)C1]

A =

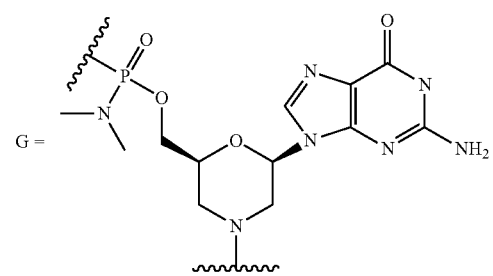 [SMILES: *N1C[C@@H](COP(*)(=O)N(C)C)O[C@@H](n2cnc3c(=O)[nH]c(N)nc32)C1]

G =

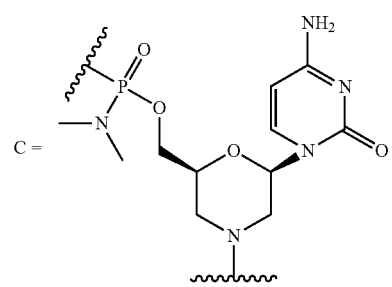 [SMILES: *N1C[C@@H](COP(*)(=O)N(C)C)O[C@@H](n2ccc(N)nc2=O)C1]

C =

TABLE 1-continued

Various embodiments of nucleotide moieties.

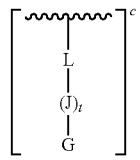

In some embodiments, the oligonucleotides described herein are unsolvated. In other embodiments, one or more of the oligonucleotides are in solvated form. As known in the art, the solvate can be any of pharmaceutically acceptable solvent, such as water, ethanol, and the like.

Although the oligonucleotides of Formulas II and IIa, are depicted in their neutral forms, in some embodiments, these oligonucleotides are used in a pharmaceutically acceptable salt form.

Peptides

The oligonucleotides provided herein include an oligonucleotide moiety conjugated to a CPP. In particular, the cell-penetrating peptide is a linear, or non-cyclic, peptide. In some embodiments, the CPP can have a theoretical positive net charge. In some embodiments, the positive net charge can be 1-12 integers. A representation of such a CPP is shown below:

wherein c is an integer from 1-12.

In some embodiments, the CPP can be an arginine-rich peptide transport moiety effective to enhance transport of the compound into cells. The transport moiety is, in some embodiments, attached to a terminus of the oligomer. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter.

The transport moieties as described above have been shown to greatly enhance cell entry of attached oligomers, relative to uptake of the oligomer in the absence of the attached transport moiety. Uptake may be enhanced at least two fold, and, in some embodiments, tenfold, relative to the unconjugated compound. In some embodiments, uptake may be enhanced at least two fold, and, in some embodiments, tenfold, relative to the CPP-Cy5.5 conjugate.

The use of arginine-rich peptide transporters (i.e., cell-penetrating peptides) are particularly useful in practicing the present disclosure. Certain peptide transporters have been shown to be highly effective at delivery of antisense compounds into primary cells including muscle cells. Furthermore, the peptide transporters described herein, when conjugated to an antisense PMO, demonstrate an enhanced ability to alter splicing of several gene transcripts.

Thus, in one aspect, provided herein is a peptide of Formula III:

$$G\text{-}(J)_t\text{-}L \qquad (III)$$

or a pharmaceutically acceptable salt thereof,
wherein
t is 5-27;
each J is, independently at each occurrence, selected from the group consisting of arginine, glycine, leucine, alanine, phenylalanine, methionine, tryptophan, lysine, glutamine, glutamic acid, serine, proline, valine, isoleucine, cysteine, tyrosine, histidine, asparagine, aspartic acid, and threonine;
wherein at least one J is arginine;
G is covalently linked by an amide bond to the carboxy-terminus of J, and G is selected from H, —C(O)C$_{1-6}$-alkyl, benzoyl, and stearoyl; and
L is —C(O)(CH$_2$)$_{1-6}$—C$_{1-6}$-heteroaromatic-(CH$_2$)$_{1-6}$C(O), which may be covalently-linked to a solid support.

In an embodiment, each J is independently selected from glycine, alanine, leucine, methionine, phenylalanine, tryptophan, lysine, glutamine, glutamic acid, serine, proline, valine, arginine, and threonine.

In another embodiment, each J is independently selected from arginine, lysine, and glutamine.

In another embodiment, each J is independently selected from glycine, leucine, alanine, phenylalanine, serine, threonine, methionine, tryptophan, glutamine, proline, lysine, arginine, and valine.

In another embodiment, each J is independently selected from arginine, isoleucine, proline, leucine, phenylalanine, and glycine.

In still another embodiment, each J is independently selected from glycine, arginine, proline, glutamic acid, serine, lysine, and leucine.

In yet another embodiment, each J is independently selected from alanine, leucine, tryptophan, lysine, threonine, valine, proline, and arginine.

In still another embodiment, L is —C(O)(CH$_2$)$_{1-6}$—C$_{1-6}$-heteroaromatic-(CH$_2$)$_{1-6}$C(O)

In another embodiment, L is

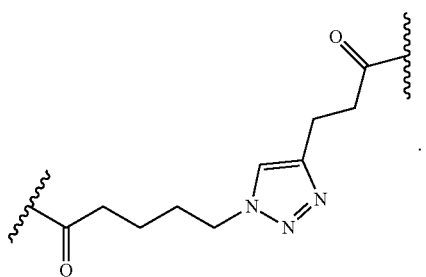 [SMILES: *C(=O)CCCCn1cc(CCC(*)=O)nn1]

In yet another embodiment, G is selected from the group consisting of H, C(O)CH$_3$, benzoyl, and stearoyl.

In still another embodiment, G is C(O)CH$_3$ or H.

In another embodiment, G is C(O)CH$_3$.

In another embodiment, G is H.

In yet another embodiment, G is covalently linked by an amide bond to the carboxy-terminus of J. In a further embodiment, L is covalently linked by an amide bond to the amino-terminus of J.

In some embodiments, the peptides described herein are unsolvated. In other embodiments, one or more of the peptides are in solvated form. As known in the art, the solvate can be any of pharmaceutically acceptable solvent, such as water, ethanol, and the like.

Although the peptides of Formula III, are depicted in their neutral forms, in some embodiments, these oligonucleotides are used in a pharmaceutically acceptable salt form.

Methods

Provided herein are methods of treating a muscle disease, a viral infection, or a bacterial infection in a subject in need thereof, comprising administering to the subject a peptide-oligonucleotide-conjugate of Formulae I, Ia, or Ib.

Accordingly, in one aspect, provided herein is a method of treating a muscle disease, a viral infection, or a bacterial infection in a subject in need thereof, comprising administering to the subject a peptide-oligonucleotide-conjugate of the present disclosure.

In one embodiment, the muscle disease is Duchenne Muscular Dystrophy.

In another embodiment, the viral infection is caused by a virus selected from the group consisting of marburg virus, ebola virus, influenza virus, and dengue virus.

In another embodiment, the bacterial infection is caused by *Mycobacterium tuberculosis*.

The subject considered herein is typically a human. However, the subject can be any mammal for which treatment is desired. Thus, the methods described herein can be applied to both human and veterinary applications.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual oligomers, and can generally be estimated based on EC$_{50}$s found to be effective in in vitro and in vivo animal models. In general, dosage is from 0.01 µg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g/kg of body weight, once or more daily, to once every 20 years.

In some embodiments, the oligonucleotide (an oligonucleotide of Formulae II or IIa) is administered alone.

In some embodiments, the oligonucleotide is administered in a therapeutically effective amount or dosage. A "therapeutically effective amount" is an amount of an oligonucleotide of Formula II or IIa that, when administered to a patient by itself, effectively treats a muscle disease, a viral infection, or a bacterial infection. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the oligonucleotide that corresponds to a therapeutically effective amount is strongly dependent on the type of disease, stage of the disease, the age of the patient being treated, and other facts.

In different embodiments, depending on the oligonucleotide of Formulae II or IIa and the effective amounts used, the oligonucleotides can modulate the expression of a gene involved in a muscle disease, a viral infection, or a bacterial infection.

While the amounts of an oligonucleotide of Formulae II or IIa should result in the effective treatment of a muscle disease, a viral infection, or a bacterial infection, the amounts, are preferably not excessively toxic to the patient (i.e., the amounts are preferably within toxicity limits as established by medical guidelines). In some embodiments, either to prevent excessive toxicity or provide a more efficacious treatment, or both, of a muscle disease, a viral infection, or a bacterial infection, a limitation on the total administered dosage is provided. Typically, the amounts considered herein are per day; however, half-day and two-day or three-day cycles also are considered herein.

Different dosage regimens may be used to treat a muscle disease, a viral infection, or a bacterial infection. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

Oligonucleotides of Formula II and IIa, or their pharmaceutically acceptable salts or solvate forms, in pure form or in an appropriate pharmaceutical composition, can be administered via any of the accepted modes of administration or agents known in the art. The oligonucleotides can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active oligonucleotide or oligonucleotides in a certain part of the intestinal tract in a delayed manner. Examples of embedded compositions that can be used are polymeric substances and waxes. The active oligonucleotides also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the conjugates described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the oligonucleotides described herein, or a pharmaceutically acceptable salt thereof, and 99% to 1% by weight of a pharmaceutically acceptable excipient. In one example, the composition will be between about 5% and about 75% by weight of a oligonucleotide described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising oligonucleotides, peptides, peptide-oligonucleotide-conjugates, or compositions of the disclosure. In some embodiments, kits comprise a peptide-oligonucleotide-conjugate according to Formulae I, Ia, or Ib, or a pharmaceutically acceptable salt thereof. In other embodiments, kits comprise an oligonucleotide according to Formulae II or IIa, or a pharmaceutically acceptable salt thereof. In still other embodiments, kits comprise a peptide according to Formula III, or a pharmaceutically acceptable salt thereof.

The phrase "package" means any vessel containing oligonucleotides or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering oligonucleotides or compositions of the disclosure to a patient. Kits also can comprise instructions for approved uses of oligonucleotides herein by regulatory agencies, such as the United States Food and Drug Administration. Kits can also contain labeling or product inserts for the oligonucleotides. The package(s) or any product insert(s), or both, may themselves be approved by regulatory agencies. The kits can include oligonucleotides in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Cell-penetrating peptides can facilitate the intracellular delivery of large therapeutically relevant molecules, including proteins and oligonucleotides. Although hundreds of CPP sequences are described in the literature derived both from nature and from rational design, the performance of any given sequence relies on it being well-matched to the cargo of interest. The present experiments focus specifically on CPPs for the delivery of phosphorodiamidate morpholino oligonucleotides (PMOs), a compelling type of antisense therapeutic that has recently been FDA approved for the treatment of Duchenne Muscular Dystrophy. Wide discrepancies in the performance of known CPPs for delivery of PMO cargo as opposed to a fluorophore cargo have been described herein. Therefore, the use of computational methods to predict which peptide sequences would perform best specifically for PMO delivery would be an efficient method for determining active CPP-PMO conjugates.

Discovering or predicting CPPs that are effective for delivering specific cargos remains an outstanding challenge. One method to predict CPP sequences is by building computational models that are trained on experimental data sets of CPPs. CPP prediction with support vector machines and N-to-1 neural networks based on physicochemical properties, amino acid composition, and dipeptide composition have been previously described. These models are trained on CPP sequences collected from several papers, which employ different experimental designs (cell lines, concentrations, etc.) and primarily use fluorescent cargoes to measure cell penetration. As a result, these models do not capture cargo-specific criterion that impact CPP choice for a given delivery problem.

Sixty-four CPP-PMO conjugates using literature CPP sequences and evaluated the conjugates in a fluorescence-based reporter assay for functional exon skipping were synthesized in order to generate a library for computational models. The exon skipping data from this library were then used to fit a random decision forest classifier to predict whether or not a given peptide would enhance exon skipping at least three fold when conjugated to a PMO. Finally, seven previously unreported peptide sequences (dubbed "PPCs") were evaluated in the reporter assay to validate the computational model. One of the computationally predicted sequences performed better for the specific delivery of PMOs than 80% of the tested literature CPPs. These results emphasize the importance of tailoring the CPP sequence to the cargo of interest, and the power of machine learning to discover peptide sequences with particular functions.

Example 1: General Method for Peptide Preparation and Purification

Fast-Flow Peptide Synthesis

Peptides were synthesized on a 0.1-mmol scale using an automated flow peptide synthesizer. ChemMatrix Rink Amide HYR resin (200 mg) was loaded into a reactor maintained at 90° C. All reagents were flowed at 80 mL/min with HPLC pumps through a stainless steel loop maintained at 90° C. before introduction into the reactor. For each coupling, 10 mL of a solution containing 0.2 M amino acid and 0.2 M HATU in DMF were mixed with 200 µL diisopropylethylamine and delivered to the reactor. Fmoc removal was accomplished using 10.4 mL of 20% (v/v) piperidine. Between each step, 15 mL of DMF were used to wash out the reactor. The final coupling was with 4-pentynoic acid, rather than an amino acid, but using the same conditions. After completion of the synthesis, the resins were washed 3 times with DCM and dried under vacuum.

Peptide Cleavage and Deprotection

Each peptide was subjected to simultaneous global side-chain deprotection and cleavage from resin by treatment with 6 mL of Reagent K (82.5% trifluoroacetic acid, 5% phenol, 5% water, 5% thioanisole, and 2.5% 1,2-ethanedithiol (EDT)). Cleavages were left at room temperature for 16 hours to ensure complete removal of Pbf. The cleavage cocktail was filtered to remove the resin and was evaporated by bubbling N2 through the mixture. Then ~35 mL of cold ether was added and the crude product was pelleted through centrifugation for three minutes. This ether trituration and centrifugation was repeated two more times. After the third wash, the pellet was redissolved in 50% water and 50% acetonitrile and lyophilized.

Peptide Purification

Solvent A: water containing 0.% TFA

Solvent B: acetonitrile containing 0.1% TFA

Lyophilized peptide was dissolved into a minimum volume of mobile phase (95% A, 5% B). The solution was loaded onto a reversed-phase HPLC column (Agilent Zorbax SB C18 column: 9.4×250 mm, 5 µm or Agilent Zorbax SB C3 column: 9.4×250 mm, 5 m) attached to a mass-based purification system. A linear gradient was run at 0.5% B/min from 5% B to 55% B. Using mass data about each fraction from the instrument, only pure fractions were pooled and lyophilized. The purity of the fraction pool was confirmed by LC-MS.

Using the protocol of Example 1, the peptides of Table 2 were synthesized.

TABLE 2

| Cell penetrating peptides | | | | |
|---|---|---|---|---|
| CPP Name | CPP Class | SEQ ID NO.: | Amino Acid Sequence | Theoretical Net Charge |
| Arginine-12 | Cationic | SEQ ID NO.: 1 | RRRRRRRRRRRR | 12 |
| MPG | Amphipathic (cationic I) | SEQ ID NO.: 2 | GLAFLGFLGAAGST MGAWSQPKKKRKV | 5 |
| Bac7 | Proline rich | SEQ ID NO.: 3 | RRIRPRPPRLPR PRPRPLPFPRPG | 9 |
| TAT | Cationic | SEQ ID NO.: 4 | RKKRRQRRR | 8 |
| Arginine-10 | Cationic | SEQ ID NO.: 5 | RRRRRRRRRR | 10 |

TABLE 2-continued

Cell penetrating peptides

| CPP Name | CPP Class | SEQ ID NO.: | Amino Acid Sequence | Theoretical Net Charge |
|---|---|---|---|---|
| DPV6 | Cationic | SEQ ID NO.: 6 | GRPRESGKKRKRKRLKP | 9 |
| S413-PVrev | Amphipathic | SEQ ID NO.: 7 | ALWKTLLKKVLKAPKKKRKV | 9 |
| HRSV | Cationic | SEQ ID NO.: 8 | RRIPNRRPRR | 6 |
| HTLV-II Rex | Cationic | SEQ ID NO.: 9 | TRRQRTRRARRNR | 8 |
| L-2 | Amphipathic | SEQ ID NO.: 10 | HARIKPTFRRLKWKYKGKFW | 9 |
| Melittin | Amphipathic | SEQ ID NO.: 11 | GIGAVLKVLTTGLPALISWIKRKRQQ | 5 |
| DPV15 | Cationic | SEQ ID NO.: 12 | LRRERQSRLRRERQSR | 6 |
| Arginine-9 | Cationic | SEQ ID NO.: 13 | RRRRRRRRR | 9 |
| Penetratin | Cationic | SEQ ID NO.: 14 | RQIKIWFQNRRMKWKK | 7 |
| Yeast GCN4 | Cationic | SEQ ID NO.: 15 | KRARNTEAARRSRARKLQRMKQ | 9 |
| PDX-1 | Cationic | SEQ ID NO.: 16 | RHIKIWFQNRRMKWKK | 8 |
| Arginine-8 | Cationic | SEQ ID NO.: 17 | RRRRRRRR | 8 |
| BMV Gag | Cationic | SEQ ID NO.: 18 | KMTRAQRRAAARRNRWTAR | 8 |
| SynB1 | Amphipathic | SEQ ID NO.: 19 | RGGRLSYSRRRFSTSTGR | 6 |
| Knotted-1 | Cationic | SEQ ID NO.: 20 | KQINNWFINQRKRHWK | 6 |
| IVV-14 | Hydrophobic | SEQ ID NO.: 21 | KLWMRWYSPTTRRYG | 4 |
| W/R | Amphipathic (cationic II) | SEQ ID NO.: 22 | RRWWRRWRR | 6 |
| Engrailed-2 | Cationic | SEQ ID NO.: 23 | SQIKIWFQNKRAKIKK | 6 |
| DPV15b | Cationic | SEQ ID NO.: 24 | GAYDLRRRERQSRLRRRERQSR | 7 |
| Yeast PrP6 | Cationic | SEQ ID NO.: 25 | TRRNKRNRIQEQLNRK | 6 |
| DPV7 | Cationic | SEQ ID NO.: 26 | GKRKKKGKLGKKRDP | 8 |
| HoxA-13 | Cationic | SEQ ID NO.: 27 | RQVTIWFQNRRVKEKK | 5 |
| AIP6 | Amphipathic (proline rich) | SEQ ID NO.: 28 | RLRWR | 3 |
| (PPR)5 | Cationic | SEQ ID NO.: 29 | PPRPPRPPRPPRPPR | 5 |
| CAYH | — | SEQ ID NO.: 30 | CAYHRLRRC | 4 |
| DPV10 | Cationic | SEQ ID NO.: 31 | SRRARRSPRHLGSG | 6 |
| (PPR)4 | Amphipathic (proline rich) | SEQ ID NO.: 32 | PPRPPRPPRPPR | 4 |
| P22 N | Cationic | SEQ ID NO.: 33 | NAKTRRHERRRKLAIER | 7 |
| DPV1047 | Cationic | SEQ ID NO.: 34 | VKRGLKLRHVRPRVTRMDV | 7 |

TABLE 2-continued

Cell penetrating peptides

| CPP Name | CPP Class | SEQ ID NO.: | Amino Acid Sequence | Theoretical Net Charge |
|---|---|---|---|---|
| SVM4 | Amphipathic (cationic) | SEQ ID NO.: 35 | LYKKGPAKKGRPPLRGWFH | 7 |
| φ21N (12-29) | Cationic | SEQ ID NO.: 36 | TAKTRYKARRAELIAERR | 5 |
| SVM3 | Amphipathic (cationic) | SEQ ID NO.: 37 | KGTYKKKLMRIPLKGT | 6 |
| (PPR)3 | Amphipathic (proline rich) | SEQ ID NO.: 38 | PPRPPRPPR | 3 |
| SVM2 | — | SEQ ID NO.: 39 | RASKRDGSWVKKLHRILE | 5 |
| Buforin 2 | Amphipathic | SEQ ID NO.: 40 | TRSSRAGLQWPVGRVHRLLRK | 7 |
| SVM1 | — | SEQ ID NO.: 41 | FKIYDKKVRTRVVKH | 6 |
| SAP | Amphipathic (proline rich) | SEQ ID NO.: 42 | VRLPPPVRLPPPVRLPPP | 3 |
| 435b | Hydrophobic | SEQ ID NO.: 43 | GPFHFYQFLFPPV | 1 |
| Pept1 | Hydrophobic | SEQ ID NO.: 44 | PLILLRLLRGQF | 2 |
| YTA2 | — | SEQ ID NO.: 45 | YTAIAWVKAFIRKLRK | 5 |
| Pep-1 | Amphipathic (cationic I) | SEQ ID NO.: 46 | KETWWETWWTEWSQPKKRKV | 2 |
| EB-1 | Amphipathic (cationic II) | SEQ ID NO.: 47 | LIRLWSHLIHIWFQNRRLKWKKK | 9 |
| Pyrrhocoricin | Proline rich | SEQ ID NO.: 48 | VDKGSYLPRPTPPRPIYNRN | 3 |
| λN(1-22) | Cationic | SEQ ID NO.: 49 | MDAQTRRRERRAEKQAQWKAAN | 4 |
| 439a | Hydrophobic | SEQ ID NO.: 50 | GSPWGLQHHPPRT | 3 |
| MAP | Amphipathic (cationic II) | SEQ ID NO.: 51 | KLALKALKALKAALKLA | 5 |
| Bip | Hydrophobic | SEQ ID NO.: 52 | IPALK | 1 |
| Bip | Hydrophobic | SEQ ID NO.: 53 | VPALR | 1 |
| pVEC | Amphipathic (I) | SEQ ID NO.: 54 | LLIILRRRIRKQAHAHSK | 8 |
| YTA4 | — | SEQ ID NO.: 55 | IAWVKAFIRKLRKGPLG | 5 |
| K-FGF + NLS | Amphipathic | SEQ ID NO.: 56 | AAVLLPVLLAAPVQRKRQKLP | 4 |
| HN-1 | Hydrophobic | SEQ ID NO.: 57 | TSPLNIHNGQKL | 2 |
| Bip | Hydrophobic | SEQ ID NO.: 58 | VPTLK | 1 |
| Bip | Hydrophobic | SEQ ID NO.: 59 | VSALK | 1 |
| VT5 | Amphipathic (beta sheet) | SEQ ID NO.: 60 | DPKGDPKGVTVTVTVTVTGKGDPKPD | 0 |
| Transportan 10 | Amphipathic (cationic II) | SEQ ID NO.: 61 | AGYLLGKINLKALAALAKKIL | 4 |

TABLE 2-continued

Cell penetrating peptides

| CPP Name | CPP Class | SEQ ID NO.: | Amino Acid Sequence | Theoretical Net Charge |
|---|---|---|---|---|
| SAP(E) | Amphipathic | SEQ ID NO.: 62 | VELPPPVELP PPVELPPP | -3 |
| CADY | Amphipathic (cationic II) | SEQ ID NO.: 63 | GLWRALWRLLR SLWRLLWRA | 5 |
| PreS2-TLM | Amphipathic | SEQ ID NO.: 64 | PLSSIFSRIGDP | 0 |

Example 2: Peptide Conjugation

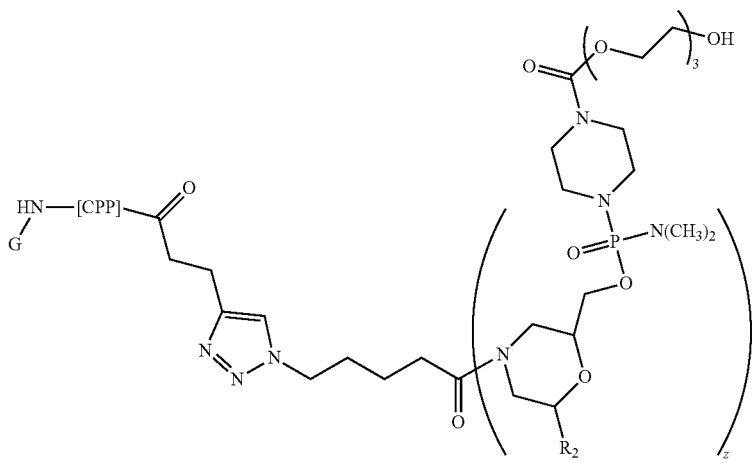

Procedure for Coupling 5-Azidopentanoic to PMO

PMO IVS-654 ($R_2$=5'-GCT ATT ACC TTA ACC CAG-3' (SEQ ID NO.: 65); z=18) (200 mg, 32 μmol) was dissolved in 600 μL DMSO. To the solution was added a solution containing 4 equivalents of 5-azidopentanoic acid (13.6 μL, 128 μmol) activated with HBTU (320 μL of 0.4 M HBTU in DMF, 128 μmol) and DIEA (22.3 μL, 128 μmol) in 244 μL DMF (Final reaction volume=1.2 mL). The reaction proceeded for 25 minutes before being quenched with 1 mL of water and 2 mL of ammonium hydroxide. The ammonium hydroxide will hydrolyze any ester formed during the course of the reaction. After 1 hour, the solution was diluted to 40 mL and purified using reversed-phase HPLC (Agilent Zorbax SB C3 column: 21.2×100 mm, 5 μm) and a linear gradient from 2 to 60% B (solvent A: water, solvent B: acetonitrile) over 58 minutes (1% B/min). Using mass data about each fraction from the instrument, only pure fractions were pooled and lyophilized. The purity of the fraction pool was confirmed by LC-MS. Lyophilization afforded 171 mg of dry powder (84% yield).

General Procedure for PMO-Peptide Conjugation by Azide/Alkyne Huisgen Cycloaddition A 20 mL scintillation vial with a septum cap was charged with peptide alkyne (1.1 μmol), ISV2-654 azide (0.95 μmol), and copper bromide (0.05 mmol). The vial was purged with nitrogen for 5 minutes to ensure the removal of oxygen before the addition of ~1 mL of DMF through the septum. The reaction mixture was vortexed for 1 minute. After 2 hours, the reaction mixture was diluted with 10 mL of 50 mM Tris (pH 8), and loaded onto reversed-phase HPLC column (Agilent Zorbax SB C3 9.4×50 mm, 5 μm). Chromatography was performed using a linear gradient from 5-45% B over 20 minutes. Solvent A: 5 mM ammonium acetate, pH=8 in water, solvent B: 5 mM ammonium acetate pH=8 in 90% acetonitrile 10% water. Using mass data about each fraction from the instrument, only pure fractions were pooled and lyophilized. The purity of the fraction pool was confirmed by LC-MS.

Example 3: Computational Design

Random forest classifier hyperparameters were optimized through grid search with classification accuracy estimated with five-fold cross validation. The selected number of features, number of trees, and maximum tree depth were five, ten, and five respectively. Performance metrics from classifier evaluation on a held-out test set of twenty sequences are given in FIG. 2A.

The performance metrics are defined below, where TP refers to true positive, TN refers to true negative, FP refers to false positive, and FN refers to false negative.

$$\text{Accuracy} = \frac{TP + TN}{TP + TN + FP + FN}$$

$$\text{Precision} = \frac{TP}{TP + FP}$$

$$\text{Recall} = \frac{TP}{TP + FN}$$

Nineteen features for each peptide sequence were calculated, one of which was peptide molecular weight. The remaining eighteen features were derived from six amino acid physicochemical descriptors, which were produced by factor analysis of 384 molecular properties calculated for 22 natural and 593 non-natural amino acids. For each peptide sequence, these six descriptors were averaged across the five N-terminal residues, the five C-terminal residues, and the entire peptide sequence.

The CPP sequences were classified as either positive or negative examples based on whether or not they exhibited above a three-fold change in eGFP fluorescence with respect to the unconjugated PMO. Forty-four sequences were used as the training set for the random forest model and twenty sequences were held out to serve as a test set to evaluate the degree to which the model properly fit the data and could successfully predict the exon skipping activity of a sequence. The performance metrics of the model are shown in FIG. 2A.

In order to validate experimentally, random peptide sequences were generated by selecting a peptide length and amino acid composition with probability proportional to the distribution observed in the training data set from the CPP library. Of the random peptides, five positive sequences were predicted to lead to above a three-fold increase in eGFP fluorescence and two were predicted to be negative sequences (NSs). More positive sequences were selected to develop novel peptide sequences for PMO delivery, which have been termed predicted PMO carriers (PPCs). These PPCs were synthesized by solid-phase peptide synthesis, conjugated to PMO IVS2-654, and purified by RP-HPLC. Results are shown in FIG. 2A and FIG. 2B.

Example 4: Flow Cytometry

In order to test the library of PMO-CPP conjugates, flow cytometry analysis of GFP fluorescence was conducted. For testing the CPPs, HeLa 654 cells were maintained in MEM supplemented with 10% (v/v) fetal bovine serum (FBS) and 1% (v/v) penicillin-streptomycin at 37° C. and 5% $CO_2$. Stocks of each PMO-CPP conjugate were prepared in phosphate-buffered serum (PBS). The concentration of the stocks was determined by measuring the absorbance at 260 nm and using an extinction coefficient of 168,700 L $mol^{-1}$ $cm^{-1}$. Cells were incubated with each respective conjugate at a concentration of 5 µM in MEM supplemented with 10% FBS and 1% penicillin-streptomycin for 22 hours at 37° C. and 5% $CO_2$. Next, the treatment media was aspirated, the cells were incubated with Trypsin-EDTA 0.25% for 15 min at 37° C. and 5% $CO_2$, washed 1× with PBS, and resuspended in PBS with 2% FBS and 2 µg/mL propidium iodide.

Figure 1E:
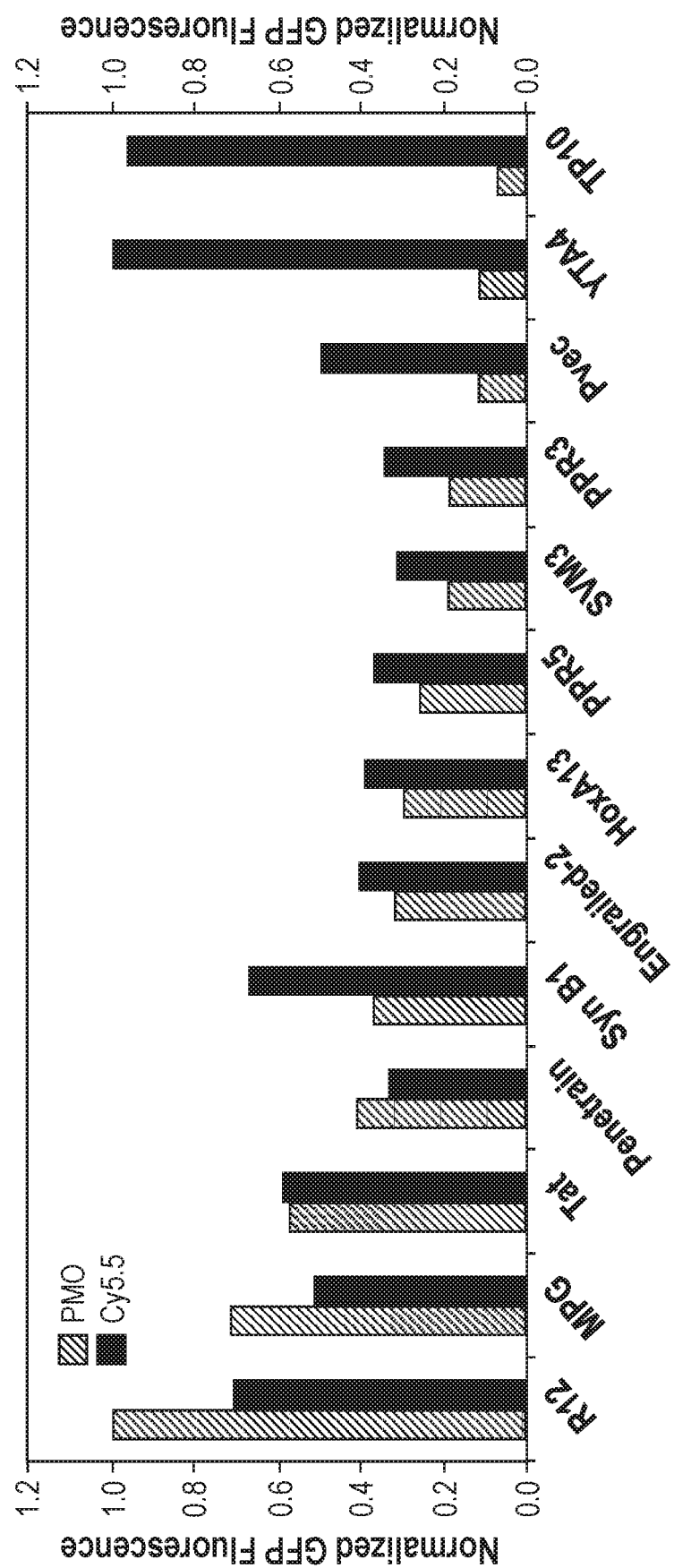
FIG. 1E Shows the comparison of thirteen CPPs with either Cy5.5 cargo or PMO IVS2-654 cargo.

Flow cytometry analysis was carried out on a BD LSRII flow cytometer. Gates were applied to the data to exclude cells that were highly positive for propidium iodide or had forward/side scatter readings that were sufficiently different from the main cell population. Each histogram contains at least 10,000 gated events. Results are shown in FIG. 1E, FIG. 2C, and Table 3.

TABLE 3 cell penetrating peptide-oligomer conjugate compared to unconjugated PMO

| CPP Name | Activity Relative to PMO | CPP Name | Activity Relative to PMO |
|---|---|---|---|
| Arginine-12 | 10.4 | P22 N | 2.4 |
| MPG | 7.5 | DPV1047 | 2.4 |
| Bac7 | 6.1 | SVM4 | 2.2 |
| TAT | 6.0 | φ21N(12-29) | 2.1 |
| Arginine-10 | 5.8 | SVM3 | 2.1 |
| DPV6 | 5.4 | (PPR)3 | 1.9 |
| S413-PVrev | 5.2 | SVM2 | 1.9 |
| HRSV | 4.9 | Buforin 2 | 1.9 |
| HTLV-II Rex | 4.7 | SVM1 | 1.7 |
| L-2 | 4.6 | SAP | 1.7 |
| Melittin | 4.5 | 435b | 1.7 |
| DPV15 | 4.3 | Pept1 | 1.7 |
| Arginine-9 | 4.2 | YTA2 | 1.5 |
| Penetratin | 4.2 | Pep-1 | 1.4 |
| Yeast GCN4 | 4.2 | EB-1 | 1.4 |
| PDX-1 | 4.1 | Pyrrhocoricin | 1.4 |
| Arginine-8 | 4.0 | λN(1-22) | 1.4 |
| BMV Gag | 3.9 | 439a | 1.3 |
| SynB1 | 3.9 | MAP | 1.3 |
| Knotted-1 | 3.8 | Bip | 1.3 |
| IVV-14 | 3.7 | Bip | 1.3 |
| W/R | 3.5 | pVEC | 1.2 |
| Engrailed-2 | 3.4 | YTA4 | 1.2 |
| DPV15b | 3.3 | K-FGF + NLS | 1.2 |
| Yeast PrP6 | 3.3 | HN-1 | 1.2 |
| DPV7 | 3.2 | Bip | 1.2 |
| HoxA-13 | 3.1 | Bip | 1.1 |
| AIP6 | 2.9 | VT5 | 0.8 |
| (PPR)5 | 2.7 | Transportan 10 | 0.8 |
| CAYH | 2.6 | SAP(E) | 0.8 |
| DPV10 | 2.5 | CADY | 0.6 |
| (PPR)4 | 2.4 | PreS2-TLM | 0.6 |

Example 5: Inhibitor Experiments

Figure 3A:
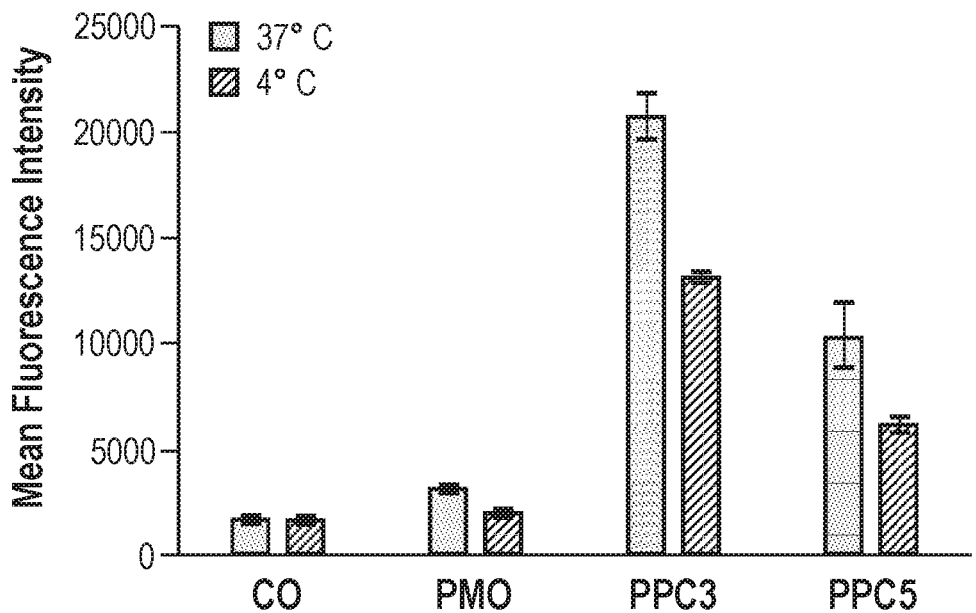
FIG. 3A Shows the effect of temperature on uptake of the PPCs.
Figure 3B:
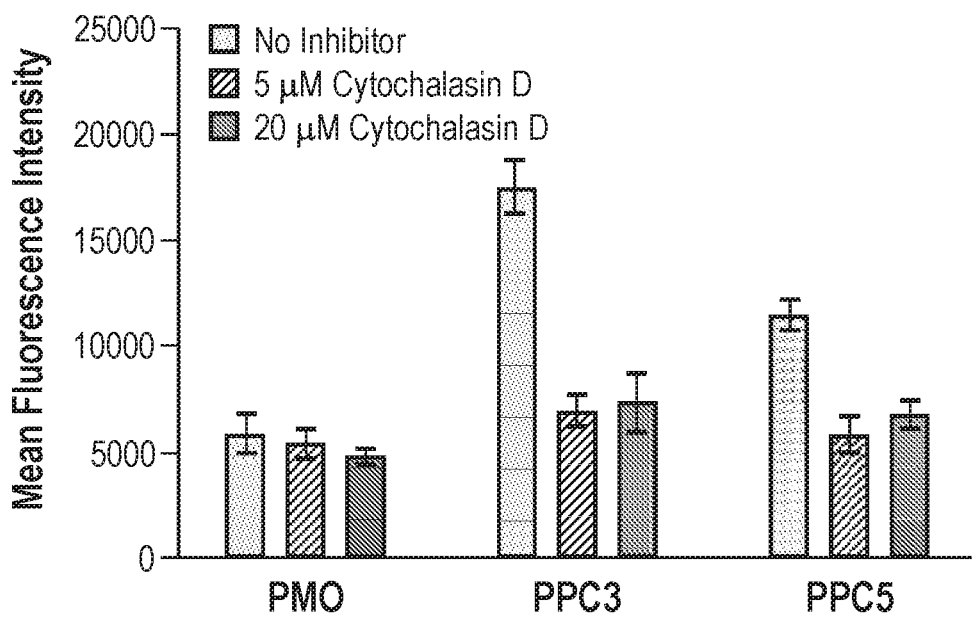
FIG. 3B Shows the effect of cytochalasin D on uptake of the PPCs. s

To inhibit a variety of endocytic mechanisms, a pulse-chase experiment was performed. Briefly, HeLa 654 cells were plated at a density of 5,000 cells per well in a 96-well plate in MEM supplemented with 10% FBS and 1% penicillin-streptomycin. The next day, the cells were treated with each inhibitor at the indicated concentration. After 30 minutes, PMO-peptide conjugate was added to each well at a concentration of 5 µM. After incubation at 37° C. and 5% $CO_2$ for 3 hours, the treatment media was replaced with fresh media (no inhibitor or PMO-peptide) and the cells were allowed to grow for another 22 hours at 37° C. and 5% $CO_2$. For the 4° C. experiments, the day after plating, the cells were pre-incubated for 30 minutes at 4° C., followed by the addition of PMO-peptide conjugate to each well at a concentration of 5 µM. After incubation at 4° C. for 3 hours, the treatment media was replaced with fresh media and the cells were allowed to grow for another 22 hours at 37° C. and 5% $CO_2$. Sample preparation and flow cytometry was then performed as described above. Each histogram contains at least 2,000 gated events, with the exception of treatment with 20 µM cytochalasin D and 200 nM wortmannin. Results are shown in FIG. 3A and FIG. 3B.

While eGFP fluorescence was relatively unchanged after pre-incubation with many of the inhibitors, pre-incubation with cytochalasin D led to a notable decrease in eGFP fluorescence. Cytochalasin D binds to the barbed, fast growing ends of actin microfilaments, which prevents assembly and disassembly of actin monomers. This affects not only the cytoskeleton of the cell, but also the ability of the membrane to ruffle and reorganize to facilitate macropinocytosis. While it is possible that the decrease in eGFP fluorescence is due to effects downstream in the exon skipping pathway, these results suggest that macropinocytosis plays a significant role in the internalization of the present conjugates.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A peptide-oligonucleotide conjugate of Formula (I):

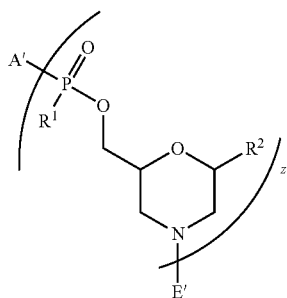

(I)

or a pharmaceutically acceptable salt thereof,
wherein:

A' is selected from —NHCH$_2$C(O)NH$_2$, —N(C$_{1-6}$-alkyl)CH$_2$C(O)NH$_2$,

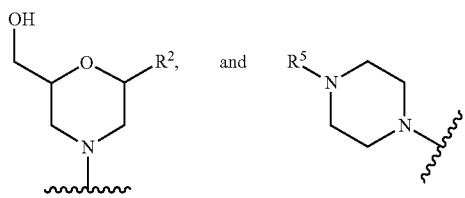

wherein
R$^5$ is —C(O)(O-alkyl)$_x$-OH, wherein x is 3-10 and each alkyl group is, independently at each occurrence, C$_{2-6}$-alkyl, or R$^5$ is selected from —C(O)C$_{1-6}$-alkyl, trityl, monomethoxytrityl, —(C$_{1-6}$-alkyl)R$^6$, —(C$_{1-6}$-heteroalkyl)-R$_6$, aryl-R$_6$, heteroaryl-R$^6$, —C(O)O—(C$_{1-6}$-alkyl)-R$^6$, —C(O)O-aryl-R$^6$, —C(O)O-heteroaryl-R$^6$, and

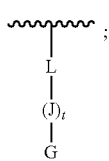;

wherein R$^6$ is selected from OH, SH, and NH$_2$, or R$^6$ is O, S, or NH, covalently linked to a solid support;

each R$^1$ is independently selected from OH and —NR$^3$R$^4$, wherein each R$^3$ and R$^4$ are, independently at each occurrence, —C$_{1-6}$-alkyl;

each R$^2$ is independently selected from H, a nucleobase, and a nucleobase functionalized with a chemical protecting-group, wherein the nucleobase, independently at each occurrence, comprises a C$_{3-6}$-heterocyclic ring selected from pyridine, pyrimidine, triazinane, purine, and deaza-purine;

z is 8-40; and

E' is selected from H, —C$_{1-6}$-alkyl, —C(O)C$_{1-6}$-alkyl, benzoyl, stearoyl, trityl, monomethoxytrityl, dimethoxytrityl, trimethoxytrityl,

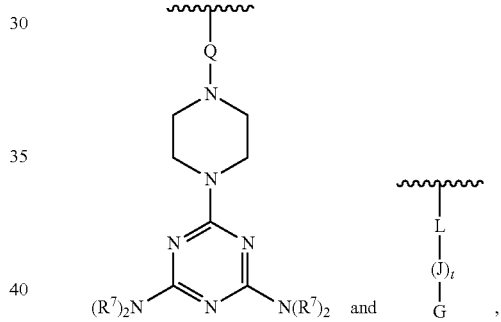

wherein

Q is —C(O)(CH$_2$)$_6$C(O)— or —C(O)(CH$_2$)$_2$S$_2$(CH$_2$)$_2$C(O)—, and

R$^7$ is —(CH$_2$)$_2$OC(O)N(R$^8$)$_2$, wherein R$^8$ is —(CH$_2$)$_6$NHC(=NH)NH$_2$, and wherein L is covalently linked by an amide bond to the amino-terminus of J, and L is —C(O)(CH$_2$)$_{1-6}$—C$_{1-6}$-heteroaromatic-(CH$_2$)$_{1-6}$C(O)—;

t is 5-27;

each J is independently at each occurrence, selected from the group consisting of arginine, glycine, leucine, alanine, phenylalanine, methionine, tryptophan, lysine, glutamine, glutamic acid, serine, proline, valine, isoleucine, cysteine, tyrosine, histidine, asparagine, aspartic acid, and threonine;

wherein at least one J is arginine;

G is covalently linked by an amide bond to the carboxy-terminus of J, and G is selected from H, —C(O)C$_{1-6}$-alkyl, benzoyl, and stearoyl; and wherein at least one of the following conditions is true:
1) A' is

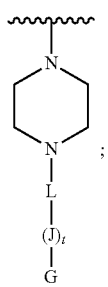

or 2) E' is

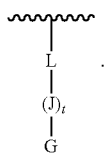

2. The peptide-oligonucleotide conjugate of claim 1, or a pharmaceutically acceptable salt thereof, wherein
A' is selected from —N($C_{1-6}$-alkyl)$CH_2$C(O)$NH_2$.

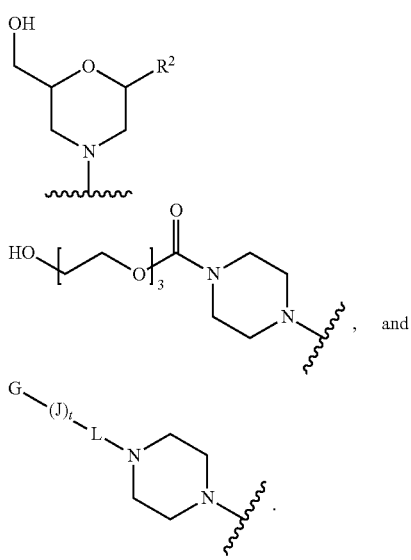

3. The peptide-oligonucleotide conjugate of claim 1, or a pharmaceutically acceptable salt thereof, wherein E' is selected from H, —C(O)$CH_3$, benzoyl, stearoyl, trityl, 4-methoxytrityl, and

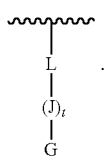

4. The peptide-oligonucleotide conjugate of claim 1, or a pharmaceutically acceptable salt thereof, wherein the peptide-oligonucleotide conjugate of Formula (I) is a peptide-oligonucleotide conjugate selected from:

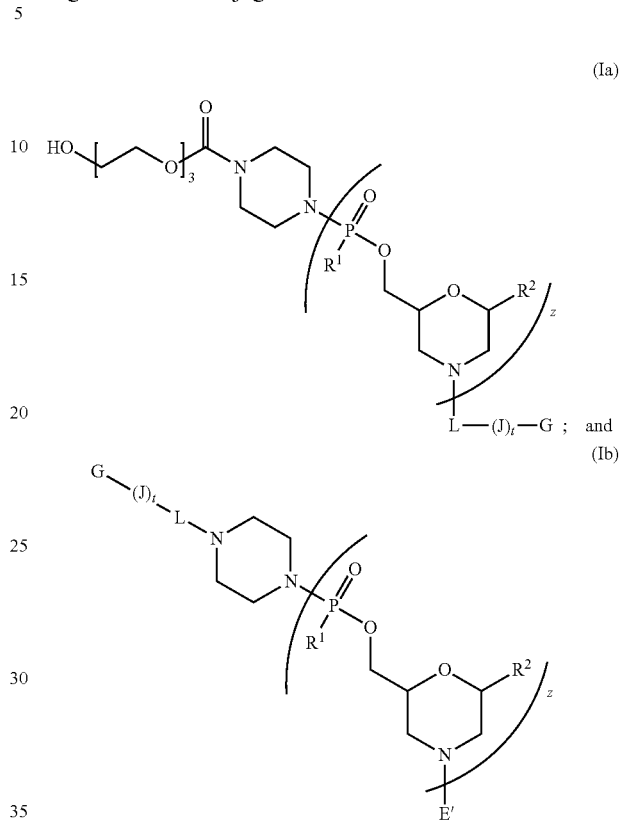

wherein E' is selected from H, $C_{1-6}$-alkyl, —C(O)$CH_3$, benzoyl, and stearoyl.

5. The peptide-oligonucleotide conjugate of claim 4, or a pharmaceutically acceptable salt thereof, wherein the peptide-oligonucleotide conjugate is of the Formula (Ia).

6. The peptide-oligonucleotide conjugate of claim 4, or a pharmaceutically acceptable salt thereof wherein the peptide-oligonucleotide conjugate is of the Formula (Ib).

7. The peptide-oligonucleotide conjugate of claim 1, or a pharmaceutically acceptable salt thereof, wherein each J is independently selected from glycine, alanine, leucine, methionine, phenylalanine, tryptophan, lysine, glutamine, glutamic acid, serine, proline, valine, arginine, and threonine.

8. The peptide-oligonucleotide conjugate of claim 1, or a pharmaceutically acceptable salt thereof, wherein each J is arginine.

9. The peptide-oligonucleotide conjugate of claim 1, or a pharmaceutically acceptable salt thereof, wherein each $R^1$ is N($CH_3$)$_2$.

10. The peptide-oligonucleotide conjugate of claim 1, or a pharmaceutically acceptable salt thereof; wherein each $R^2$ is a nucleobase, independently at each occurrence, selected from adenine, guanine, cytosine, 5-methyl-cytosine, thymine, uracil, and hypoxanthine.

11. The peptide-oligonucleotide conjugate of claim 1, or a pharmaceutically acceptable salt thereof, wherein L is —C(O)($CH_2$)$_{1-6}$-triazole-($CH_2$)$_{1-6}$C(O)—.

12. The peptide-oligonucleotide conjugate of claim 1, or a pharmaceutically acceptable salt thereof; wherein L is

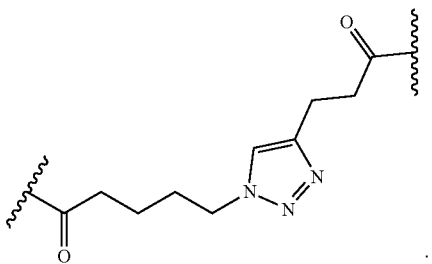 [SMILES: *C(=O)CCCCn1cc(CCC(*)=O)nn1]

13. The peptide-oligonucleotide conjugate of claim 1, or a pharmaceutically acceptable salt thereof, wherein G is selected from H, C(O)CH₃, benzoyl, and stearoyl.

14. The peptide-oligonucleotide conjugate of claim 1, or a pharmaceutically acceptable salt thereof, wherein G is —C(O)CH₃.

15. The peptide-oligonucleotide conjugate of claim 1, or a pharmaceutically acceptable salt thereof, wherein -(J)$_r$- is KQPRIPKRKK (SEQ ID NO.: 66), LKKRRKLPKKKPIRNEQ (SEQ ID NO.: 67), KKYRGRKRHPR (SEQ ID NO.: 68), APKRKKLKKRF (SEQ ID NO.: 69), GRAARAPGRRKQ, RRRRRRRRRRRR (SEQ ID NO.: 1), GLAFIGFLGAAGSTMGAWSQPKKKRKV (SEQ ID NO.: 2), RRIRPRPPRLPRPRPRPLPFPRPG (SEQ ID NO.: 3), RKKRRQRRR (SEQ ID NO.: 4), RRRRRRRRR (SEQ ID NO.: 5), GRPRESGKKRKRKRLKP (SEQ ID NO.: 6), ALWKTLLKKVLKAPKKKRKV (SEQ ID NO.: 7), RRIPNRRPRR (SEQ ID NO.: 8), TRRQRTRRARRNR (SEQ ID NO.: 9), HARIKPTFRRLKWKYKGKFW (SEQ ID NO.: 10), GIGAVLKVLTTGLPALISWIKRKRQQ (SEQ ID NO.: 11), LRRERQSRLRRERQSR(SEQ ID NO.: 12), RRRRRRRRR (SEQ ID NO.: 13), RQIKIWFQNRRMKWKK (SEQ ID NO.: 14), KRARNTEAARRSRARKLQRMKQ (SEQ ID NO.: 15) RHIKIWFQNRRMKWKK (SEQ ID NO.: 16), RRRRRRRR (SEQ ID NO.: 17), KMTRAQRRAAARRNRWTAR (SEQ ID NO.: 18), RGGRLSYSRRRFSTSTGR (SEQ ID NO.: 19), KQINNWFINQRKRHWK (SEQ ID NO.: 20), KLWMRWYSPTTRRYG (SEQ ID NO.: 21), RRWWRRWRR (SEQ ID NO.: 22), SQIKIWFQNKRAKIKK (SEQ ID NO.: 23), GAYDLRRRERQSRLRRRERQSR (SEQ ID NO.: 24), TRRNKRNRIQEQLNRK (SEQ ID NO.: 25), GKRKKKGKLGKKRDP (SEQ ID NO.: 26), RQVTIWFQNRRVKEKK (SEQ ID NO.: 27), RLRWR (SEQ ID NO.: 28) PPRPPRPPRPPRPPR (SEQ ID NO.: 29), CAYHRLRRC (SEQ ID NO.: 30), SRRARRSPRHLGSG (SEQ ID NO.: 31), PPRPPRPPRPPR (SEQ ID NO.: 32), NAKTRRHERRRKLAIER (SEQ ID NO.: 33), VKRGLKLRHVRPRVTRMDV (SEQ ID NO.: 34), LYKKGPAKKGRPPLRGWFH (SEQ ID NO.: 35), TAKTRYKARRAELIAERR (SEQ ID NO.: 36), KGTYKKKLMRIPLKGT (SEQ ID NO.: 37), PPRPPRPPR (SEQ ID NO.: 38), RASKRDGSWVKKLHRILE (SEQ ID NO.: 39), TRSSRAGLQWPVGRVHRLLRK (SEQ ID NO.: 40), FKIYDKKVRTRVVKH (SEQ ID NO.: 41), VRLPPPVRLPPPVRLPPP (SEQ ID NO.: 42), PLILLRLLRGQF (SEQ ID NO.: 44), YTAIAWVKAFIRKLRK (SEQ ID NO.: 45), KETWWETWTEWSQPKKRKV (SEQ ID NO.: 46), LIRLWSHLIHIWFQNRRLKWKKK (SEQ ID NO.: 47), VDKGSYLPRPTPPRPIYNRN (SEQ ID NO.: 48), MDAQTRRRERRAEKQAQWKAAN (SEQ ID NO.: 49), GSPWGLQHHPPRT (SEQ ID NO.: 50), VPALR (SEQ ID NO.: 53), LLIILRRRIRKQAHAHSK (SEQ ID NO.: 54), IAWVKAFIRKLRKGPLG (SEQ ID NQ 55) or AAVLLPVLLAAPVQRKRQKLP (SEQ ID NO.: 56).

16. The peptide-oligonucleotide conjugate of claim 1, or a pharmaceutically acceptable salt thereof, wherein -(J)$_r$- is KKYRGRKRHPR (SEQ ID NO.: 68), APKRKKLKKRF (SEQ ID NO.: 69), RRRRRRRRRRRR (SEQ ID NO.: 1), GLAFLGFLGAAGSTMGAWSQPKKKRKV (SEQ ID NO. 2), RRIRPRPPRLPRPRPRPLPFPRPG (SEQ ID NO.: 3), RKKRRQRRR (SEQ ID NO.: 4), RRRRRRRRR (SEQ ID NO.: 5), GRPRESGKKRKRKRLKP (SEQ ID NO.: 6), or ALWKTLLKKVLKAPKKKRKV (SEQ ID NO.: 7).

17. A pharmaceutical composition comprising a compound of claim 1, or a pharmaceutically acceptable salt thereof, and at least one pharmaceutically acceptable carrier.

18. The peptide-oligonucleotide conjugate of claim 1, or a pharmaceutically acceptable salt thereof, wherein the peptide-oligonucleotide conjugate is of Formula (IV):

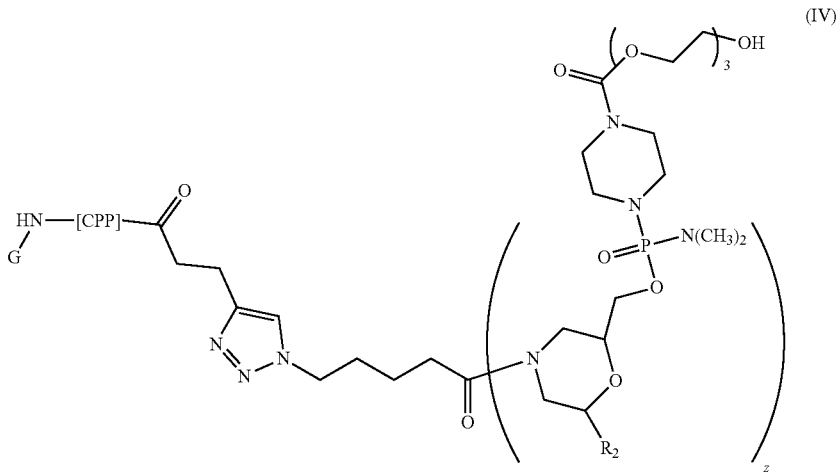

wherein
R² is a nucleobase, independently at each occurrence, selected from adenine, guanine, cytosine, 5-methyl-cytosine, thymine, uracil, and hypoxanthine;
z is 8-40;
CPP is KKYRGRKRHPR (SEQ ID NO.: 68); and
G is H or —C(O)CH₃.

19. The peptide-oligonucleotide conjugate of claim 1, or a pharmaceutically acceptable salt thereof, wherein the peptide-oligonucleotide conjugate is of Formula (IV):

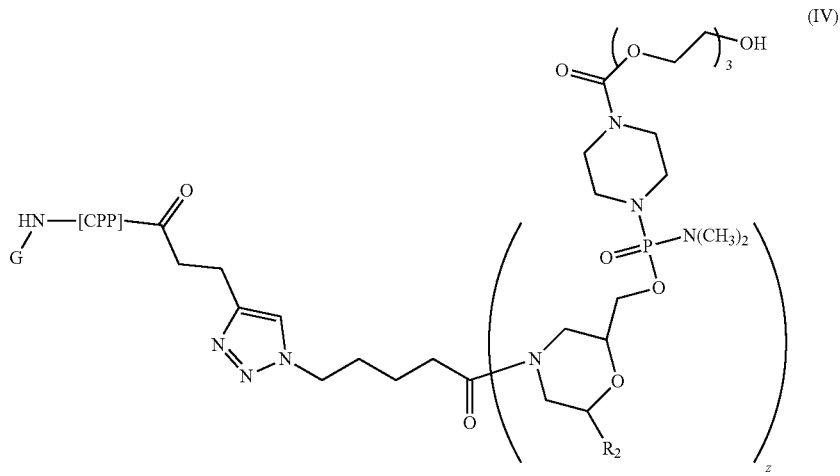

wherein
R² is a nucleobase, independently at each occurrence, selected from adenine, guanine, cytosine, 5-methyl-cytosine, thymine, uracil, and hypoxanthine;
z is 8-40;
CPP is APKRKKLKKRF (SEQ ID NO.: 69); and
G is H or —C(O)CH₃.

* * * * *

SEQUENCE LISTING

```
<160> NUMBER OF SEQ ID NOS: 72

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg Arg Arg Arg Arg Arg Arg Arg Arg
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Lys Lys Arg Arg Gln Arg Arg Arg
1               5
```

```
<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg Arg Arg Arg Arg Arg Arg
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Arg Pro Arg Glu Ser Gly Lys Lys Arg Lys Arg Lys Arg Leu Lys
1               5                   10                  15

Pro

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Trp Lys Thr Leu Leu Lys Lys Val Leu Lys Ala Pro Lys Lys
1               5                   10                  15

Lys Arg Lys Val
            20

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Ile Pro Asn Arg Arg Pro Arg Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Arg Arg Gln Arg Thr Arg Arg Ala Arg Arg Asn Arg
1               5                   10

<210> SEQ ID NO 10
<211> LENGTH: 20
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Ala Arg Ile Lys Pro Thr Phe Arg Arg Leu Lys Trp Lys Tyr Lys
1               5                   10                  15

Gly Lys Phe Trp
            20

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Arg Arg Glu Arg Gln Ser Arg Leu Arg Arg Glu Arg Gln Ser Arg
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Arg Arg Arg Arg Arg Arg Arg
1               5

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 22
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 15

Lys Arg Ala Arg Asn Thr Glu Ala Ala Arg Ser Arg Ala Arg Lys
1               5                   10                  15

Leu Gln Arg Met Lys Gln
            20

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg His Ile Lys Ile Trp Phe Gln Asn Arg Arg Met Lys Trp Lys Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Arg Arg Arg Arg Arg
1               5

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Met Thr Arg Ala Gln Arg Arg Ala Ala Ala Arg Arg Asn Arg Trp
1               5                   10                  15

Thr Ala Arg

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly Gly Arg Leu Ser Tyr Ser Arg Arg Arg Phe Ser Thr Ser Thr
1               5                   10                  15

Gly Arg

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Lys Gln Ile Asn Asn Trp Phe Ile Asn Gln Arg Lys Arg His Trp Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Leu Trp Met Arg Trp Tyr Ser Pro Thr Thr Arg Arg Tyr Gly
1               5                   10                  15

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Trp Trp Arg Arg Trp Arg Arg
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gln Ile Lys Ile Trp Phe Gln Asn Lys Arg Ala Lys Ile Lys Lys
1               5                   10                  15

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Arg Arg Asn Lys Arg Asn Arg Ile Gln Glu Gln Leu Asn Arg Lys
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Lys Arg Lys Lys Lys Gly Lys Leu Gly Lys Lys Arg Asp Pro
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Gln Val Thr Ile Trp Phe Gln Asn Arg Arg Val Lys Glu Lys Lys
1               5                   10                  15

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Leu Arg Trp Arg
1               5

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Pro Arg Pro Pro Arg Pro Pro Arg Pro Arg Pro Pro Arg
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Ala Tyr His Arg Leu Arg Arg Cys
1               5

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 31

Ser Arg Arg Ala Arg Arg Ser Pro Arg His Leu Gly Ser Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Pro Arg Pro Pro Arg Pro Pro Arg Pro Pro Arg
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Ala Lys Thr Arg Arg His Glu Arg Arg Arg Lys Leu Ala Ile Glu
1               5                   10                  15

Arg

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Lys Arg Gly Leu Lys Leu Arg His Val Arg Pro Arg Val Thr Arg
1               5                   10                  15

Met Asp Val

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Tyr Lys Lys Gly Pro Ala Lys Lys Gly Arg Pro Pro Leu Arg Gly
1               5                   10                  15

Trp Phe His

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 36

Thr Ala Lys Thr Arg Tyr Lys Ala Arg Arg Ala Glu Leu Ile Ala Glu
1               5                   10                  15

Arg Arg

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Gly Thr Tyr Lys Lys Lys Leu Met Arg Ile Pro Leu Lys Gly Thr
1               5                   10                  15

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Pro Arg Pro Pro Arg Pro Pro Arg
1               5

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ala Ser Lys Arg Asp Gly Ser Trp Val Lys Lys Leu His Arg Ile
1               5                   10                  15

Leu Glu

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Arg Ser Ser Arg Ala Gly Leu Gln Trp Pro Val Gly Arg Val His
1               5                   10                  15

Arg Leu Leu Arg Lys
            20

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 41

Phe Lys Ile Tyr Asp Lys Lys Val Arg Thr Arg Val Val Lys His
1               5                   10                  15

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Arg Leu Pro Pro Pro Val Arg Leu Pro Pro Pro Val Arg Leu Pro
1               5                   10                  15

Pro Pro

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Pro Phe His Phe Tyr Gln Phe Leu Phe Pro Pro Val
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Leu Ile Leu Leu Arg Leu Leu Arg Gly Gln Phe
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Thr Ala Ile Ala Trp Val Lys Ala Phe Ile Arg Lys Leu Arg Lys
1               5                   10                  15

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 46

Lys Glu Thr Trp Trp Glu Thr Trp Trp Thr Glu Trp Ser Gln Pro Lys
1               5                   10                  15

Lys Arg Lys Val
            20

<210> SEQ ID NO 47
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Asp Lys Gly Ser Tyr Leu Pro Arg Pro Thr Pro Pro Arg Pro Ile
1               5                   10                  15

Tyr Asn Arg Asn
            20

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Pro Trp Gly Leu Gln His His Pro Pro Arg Thr
1               5                   10

<210> SEQ ID NO 51
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 51

Lys Leu Ala Leu Lys Ala Leu Lys Ala Leu Lys Ala Ala Leu Lys Leu
1               5                   10                  15

Ala

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Pro Ala Leu Lys
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Pro Ala Leu Arg
1               5

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Leu Ile Ile Leu Arg Arg Arg Ile Arg Lys Gln Ala His Ala His
1               5                   10                  15

Ser Lys

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ala Trp Val Lys Ala Phe Ile Arg Lys Leu Arg Lys Gly Pro Leu
1               5                   10                  15

Gly

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Ala Ala Val Leu Leu Pro Val Leu Leu Ala Ala Pro Val Gln Arg Lys
1               5                   10                  15

Arg Gln Lys Leu Pro
            20

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ser Pro Leu Asn Ile His Asn Gly Gln Lys Leu
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Pro Thr Leu Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Val Ser Ala Leu Lys
1               5

<210> SEQ ID NO 60
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 61

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Glu Leu Pro Pro Pro Val Glu Leu Pro Pro Val Glu Leu Pro
1               5                   10                  15

Pro Pro

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Leu Trp Arg Ala Leu Trp Arg Leu Leu Arg Ser Leu Trp Arg Leu
1               5                   10                  15

Leu Trp Arg Ala
            20

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Leu Ser Ser Ile Phe Ser Arg Ile Gly Asp Pro
1               5                   10

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gctattacct taacccag                                                 18

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 66

Lys Gln Pro Arg Ile Pro Lys Arg Lys Lys
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Lys Lys Arg Arg Lys Leu Pro Lys Lys Pro Ile Arg Asn Glu
1               5                   10                  15

Gln

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Lys Tyr Arg Gly Arg Lys Arg His Pro Arg
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Pro Lys Arg Lys Lys Leu Lys Lys Arg Phe
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Arg Ala Ala Arg Ala Pro Gly Arg Arg Lys Gln
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His Asp Leu Pro Lys Gly Gly
1               5
```

```
<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Gly Ser His Arg Arg Leu
1               5
```